(12) United States Patent
Hoeg-Moller et al.

(10) Patent No.: US 8,765,185 B2
(45) Date of Patent: Jul. 1, 2014

(54) GRANULES FOR PHARMACEUTICAL PREPARATIONS, METHODS AND APPARATUS FOR THEIR PRODUCTION

(75) Inventors: Carsten Hoeg-Moller, Malov (DK); Crilles Casper Larsen, Mex (CH); Jorgen Wittendorff, Hvidovre (DK); Birgitte Nissen, Glostrup (DK); Kenneth Manby Pedersen, Lejre (DK); Tue Hansen, Hvidovre (DK); Helle Poulsen, Lyngby (DK)

(73) Assignee: Ferring B.V., Hoofdorp (NL)

( * ) Notice: Subject to any disclaimer, the term of this patent is extended or adjusted under 35 U.S.C. 154(b) by 0 days.

(21) Appl. No.: 13/516,145

(22) PCT Filed: Dec. 15, 2010

(86) PCT No.: PCT/EP2010/069733
§ 371 (c)(1),
(2), (4) Date: Oct. 8, 2012

(87) PCT Pub. No.: WO2011/073245
PCT Pub. Date: Jun. 23, 2011

(65) Prior Publication Data
US 2013/0022681 A1    Jan. 24, 2013

(30) Foreign Application Priority Data
Dec. 18, 2009 (EP) .................................... 09179877

(51) Int. Cl.
*A61K 9/16* (2006.01)
*A61P 1/00* (2006.01)
*A61P 29/00* (2006.01)
*C07C 229/64* (2006.01)
*A61K 31/606* (2006.01)

(52) U.S. Cl.
USPC ........... 424/490; 427/2.14; 514/166; 562/453

(58) Field of Classification Search
None
See application file for complete search history.

(56) References Cited

U.S. PATENT DOCUMENTS

| | | | |
|---|---|---|---|
| 4,720,473 A * | 1/1988 | Welch et al. | ..................... 502/21 |
| 5,544,426 A | 8/1996 | Yoshida et al. | |
| 6,962,717 B1 * | 11/2005 | Huber et al. | ................... 424/490 |
| 8,282,955 B2 | 10/2012 | Jepsen | |
| 2007/0043004 A1 | 2/2007 | Jepsen | |

FOREIGN PATENT DOCUMENTS

| | | |
|---|---|---|
| JP | 07-027476 A | 1/1995 |
| WO | WO 97/23199 | 7/1997 |
| WO | WO2005063256 * | 7/2005 |

OTHER PUBLICATIONS

Hagsten et al., "Identifying sources of batch to batch variation in processability," Power Technology, vol. 183, No. 2, pp. 213-219, Mar. 18, 2008.

Thommes et al., "Use of kappa-carrageenan as alternative aid to microcrystalline cellulose in extrusion/spheronisation. II. Influence of drug and filler type," European Journal of Pharmaceutics and Biopharmaceutics, vol. 63, No. 1, pp. 68-75, May 1, 2006.

International Search Report issued on Jun. 24, 2011 in application No. PCT/EP2010/069733.

* cited by examiner

*Primary Examiner* — Robert A Wax
*Assistant Examiner* — Randeep Singh
(74) *Attorney, Agent, or Firm* — Foley & Lardner LLP

(57) ABSTRACT

Disclosed are improved granular pharmaceutical preparations, together with improved methods and apparatus for preparation of granules for use in such preparations. Such methods are especially useful for making granules for solid oral dose pharmaceutical preparations, and are particularly suited to the production of granules comprising 5-aminosalicylic acid (5-ASA) for the treatment of inflammatory bowel disease. The granules exhibit a more sharply peaked length distribution, and hence aspect ratio distribution, and have a consequently much sharper dissolution profile after further processing.

29 Claims, 13 Drawing Sheets

GRANULES FOR PHARMACEUTICAL PREPARATIONS, METHODS AND APPARATUS FOR THEIR PRODUCTION

FIELD OF THE INVENTION

The present invention relates to improved granular pharmaceutical preparations, together with improved methods and use of an apparatus for preparation of granules. Such methods are especially useful for making solid oral dose pharmaceutical preparations, for instance those comprising granules having an active pharmaceutical ingredient of which the release rate needs to be predetermined (controlled) and are particularly suited to the production of granules comprising 5-aminosalicylic acid (5-ASA) for the treatment of inflammatory bowel disease.

BACKGROUND OF THE INVENTION

Many drugs are commonly employed in a granular form for preparing medical formulations, e.g. solid oral dosage forms. Beside the drug, the granules may comprise excipients such as surfactants, diluents, or disintegrating agents. Granules containing active pharmaceutical ingredients (API) can be coated subsequent to the granulation. By careful choice of the coating it is possible to control how fast and in what part of the digestive system the drug is released. In addition to the coating, controlling the physical characteristics of granules, such as size, roughness, morphology and porosity, is important as these parameters at least partly determine the amount of coating to be used.

Several approaches exist to produce granules of desired properties. These approaches generally involve an initial step of manufacturing granules followed by a unit operation aimed at sorting the produced granules according to size, in order to obtain only those granules within a required size range. Granulates can be produced by either building up particles from an initial seed or by breaking down a larger material into smaller sized particles. Often, cylinder-shaped granules are subjected to a spheronisation process, which produces spherically shaped particles, i.e. particles which for instance roll randomly as there is not or no longer just a single axis around which the particle can roll. A non-spheronised cylinder-shaped granule is characterised by the presence of a single axis around which the granule can roll. In the art, spheronised granules may also be referred to as pelletised granules or pellets. Dedicated apparatuses exist for spheronising or pelletising granules.

Typical operations employed in sorting the granules (spheronised or not) are fluidised beds or various types of sieves. However, the currently utilised procedures suffer from a number of weaknesses as will be discussed below.

WO2001/03089 describes devices for sorting pharmaceutical particles based on fluidisation principles. The housing chambers employed in these devices are equipped with rotating filters intended to retain particles larger than a desired minimum while the rotation of the filter portions will prevent clogging of the filter with (undesired) fine particles unavoidably formed during the preparation process. Application of fluidised beds for separation of particles is mainly useful for separating particles with aspect ratios close to 1, as the particles will tend to align with the fluidising stream in a way to minimise friction, i.e. longer particles can generally not be effectively separated from shorter particles with comparable widths.

US2004/0033266 discloses methods to obtain pharmaceutical particles of so-called monomodal size distributions. This is achieved by ultrasonicating large agglomerated particles resting on a screen with a mesh aperture size defining the intended particle size. The ultrasonication will break down the agglomerates into smaller particles which will then pass through the apertures and be collected on another screen with smaller holes. The methods are optimally suited for crystal agglomerates, which are held together by electrostatic interactions. The methods are much less suited for more complex types of particles or granulates, or those with aspect ratios significantly different from 1.

US2005/0269433 discloses integrated processes for producing granules from dry powders. Granulates produced in an early step of the process are milled and sorted in an intermediate, semi-dry state which is advantageous when the intermediate is size separated using screens or sieves. However, size separation through sieves has a problem similar to that of fluidised beds: particles can pass through the holes if their smallest dimensions are below those of the holes, and all but very long particles will eventually pass through the sieve. Accordingly, sieving methods fail to discriminate moderate to high-aspect-ratio particles from low-aspect-ratio particles.

Some previous methods for production of drug-containing granules, such as those described in application WO2003/032952, rely on the extrusion of a wet mass containing the drug and a suitable binder through a screen with a desired size of holes followed by drying and milling to produce a granulate. Separation according to size is then typically performed using sieves. The sieves are arranged to mechanically vibrate to enhance the probability that long granules will pass the sieve whilst moving through the sieve in their length direction. The sieved granulates in this class of process are as a consequence thereof generally observed to possess a relatively wide granule length distribution. Such a phenomenon is due to the above-noted characteristics of sieving methods. These distributions are nevertheless generally regarded as an acceptable limitation by those skilled in the art. As the sieve cannot discriminate on the basis of the lengths of the granules, it follows that the distributions are effectively width distributions. This has for a long period of time not been recognized in this field.

SUMMARY OF THE INVENTION

According to a first aspect of the present invention there is provided a pharmaceutical preparation comprising granules of which each has an active pharmaceutical ingredient and of which each has a predetermined axis and the same predetermined cross-sectional profile, wherein at least 80% by number of those granules, preferably 85%, most preferably 90% have an aspect ratio less than 2.2, preferably less than 2.1, most preferably less than 2. Each of these percentages is understood to embrace percentages within plus/minus 10%. At least 80% is therefore also considered to include 70%. It is possible that each of those granules has the same active pharmaceutical ingredient.

It is further also possible that those granules form at least 10% by number, 30% by number, 50% by number, 70% by number, 90% by number, or even 100% by number of the pharmaceutically active granules of a single dose of the pharmaceutical preparation.

The granules referred to above are considered to be non-spheronised.

Spheronised granules are considered to have sphere-like shapes and no angular or edge-like features. Often, a spheronised granule rolls randomly as there is not or no longer just a single axis around which the granules can roll. Non-spheronised granules possess angular or edge-like features to the extent that rolling around more than one axis is not possible.

Preferred embodiments of the first aspect of the invention are provided wherein at least 80% by number of those granules, preferably 90%, most preferably 95% have an aspect ratio greater than 0.7, preferably greater than 0.9, most preferably greater than 1.0. Presently preferred embodiments of the first aspect of the invention are provided wherein those granules have a median aspect ratio above 1.0, preferably above 1.1, most preferably above 1.2, and below 1.7, preferably below 1.6, most preferably below 1.5. Preferred embodiments of the first aspect of the invention are provided wherein those granules have a span of the aspect ratio less than 0.9, preferably less than 0.8, more preferably less than 0.7, even more preferably less than 0.6, most preferably less than 0.5.

It is preferable that at least one of the numerical descriptions provided above applies to all the granules of the preparation, or where applicable, at least to those having an aspect ratio greater than 1.

In each case, such embodiments are able to exhibit a more controlled and reproducible dissolution profile, that is, a greater majority of granules dissolve within a given time window after immersion in solvent, and a smaller proportion of granules dissolve outside this window. Such embodiments can release the majority of their active ingredient after a well-defined interval and are thus especially suited to applications where a well defined release after immersion in a solvent is required, such as in oral dose pharmaceuticals.

Further, pharmacologists prefer to have a well-defined and preferably narrow aspect ratio distribution, so that further processing, transporting, etc. can more easily be modeled and present less fluctuations which would otherwise be caused by some of the extremely large (or small) granules in the tails of the distribution.

Preferred embodiments of the first aspect of the invention are provided wherein the smallest cross-sectional dimension is between 0.25 mm and 2.5 mm, preferably between 0.5 mm and 2 mm, most preferably between 0.6 mm and 1.8 mm. In a very suitable embodiment, the smallest cross-sectional dimension is fixed at 0.95 mm Such embodiments are particularly suitable for the production of convenient dose forms including oral dose forms such as tablets, sachets and filled capsules.

Possible dosage forms which are envisaged by the present application are—in addition to the above-mentioned granules—tablets, capsules, sachets or pills. The granules can be used as such as a preferred dosage form, can be filled into capsules or sachets or can be further compressed into tablets or pills.

Further dosage forms which are also encompassed by the present application are drinks or syrups, elixirs, tinctures, suspensions, solutions, hydrogels, films, lozenges, chewing gums, orally disintegrating tablets, mouth-washes, toothpaste, lip balms, medicated shampoos, nanosphere suspensions and microsphere tablets, as well as aerosols, inhalers, nebulisers, smoking or freebase powder forms and dosage forms for topical application like creams, gels, liniments or balms, lotions, ointments, ear drops, eye drops and skin patches.

Further encompassed are suppositories which can be used e.g. rectally or vaginally. All these dosage forms are well-known to a person skilled in the art.

Preferred dosage forms according to the present invention are granules, coated granules, tablets, pellets, suppositories and emulsions. Even more preferred are granules and tablets. Most preferred embodiments of the present invention are represented by granules, either per se or filled in e.g. a sachet or a capsule or granules further processed to a tablet or pill. The granules of the present invention can all be further processed (e.g. dissolved), as late as shortly before administration, into any one of the above-mentioned dosage forms.

In the following, the present specification will focus on the description of "granules". However, whenever reference is made to "granules" this term shall encompass all further possible dosage forms as known to a person skilled in the art and in particular those as mentioned above as well.

Preferred embodiments of the first aspect of the invention are provided wherein the granules comprise one or more active pharmaceutical ingredients and, optionally, one or more pharmaceutically acceptable excipients, such as fillers, binders, etc.

The granules of the present invention can comprise any possible active ingredient which shall be formulated into a pharmaceutical composition. As the present invention is concerned in particular with the provision of improved properties of the resultant granules—independent of the actual pharmaceutical ingredient used—the invention does not depend on the selection of the actual active ingredient.

Just as an example, possible active ingredients in that context could be selected from anti-inflammatory compounds, anti-cancer compounds, anti-diabetes compounds, cardiovascular compounds like compounds for the treatment of high blood pressure, antibiotics, compounds for the treatment of infertility and compounds for the treatment of neurodegenerative disorders.

In a particularly preferred embodiment, the active ingredient would be an ingredient which should be delivered with a controlled, e.g. a delayed release. That is, the granules of the present invention comprising such an active ingredient might be provided with a coating, or at least a number of those granules might be provided with a coating. Thus, in a preferred embodiment the present invention is directed to granules with coatings and in particular to granules comprising active ingredients which shall be released in a controlled manner, whereby these granules have a coating.

More preferred, this coating is a pharmacologically acceptable coating and it is particularly preferred that the coating is an enteric coating, a prolonged release coating or a delayed release coating; all such coatings are well known to a person skilled in the art.

As examples, but by no means restricting the present invention, active ingredients which could be provided in such granules for controlled release, which comprise a coating, could be selected from nateglinide)(Starlix®), metoprolol (Seloken ZOK®) and esomeprazole (Nexium®).

Even more preferred, the present invention encompasses ingredients which are anti-inflammatory pharmaceutical ingredients. Particularly preferred are aminosalicylic acid or pharmacologically acceptable salts or esters thereof, thus being encompassed by the scope of the present claims. Even further preferred embodiments of the invention are provided, wherein the aminosalicylic acid is 5'-aminosalicylic acid (5-ASA). This pharmaceutical product is often referred to as PENTASA, of which a tablet (500) would, for instance, contain 500 mg 5-ASA. Non-medical ingredients are micro crystalline cellulose, ethylcellulose, magnesium stearate, povidone, and talc.

In that context, whenever reference is made in the following to a "pharmaceutical ingredient" or an "active ingredient", it shall be noted that both terms can be used interchangeably; both always encompass the possibility of using a pharmacologically acceptable salt or ester thereof.

Such embodiments are advantageous in improving the integrity of the dose form in manufacture, storage and use.

Preferred embodiments of the first aspect of the invention are provided wherein the pharmaceutical preparation is suitable for treating inflammatory bowel disease. Further preferred embodiments of the first aspect of the invention are provided wherein the pharmaceutical preparation is suitable for treating ulcerative colitis, Crohn's disease, dyspepsia, high blood pressure, diabetes type I or II, neurodegenerative disorders, inflammatory disorders, cardiovascular disorders, or cancer. As mentioned above, any active ingredient can be formulated by the present invention; thus, the active ingredient does not limit the scope thereof, which is defined only by the scope of the claims.

Such embodiments are of particular utility and exhibit improved properties when compared with other commonly-available treatments for such conditions.

Preferred embodiments of the first aspect of the invention are provided wherein the granules are compressed into a tablet. Other preferred embodiments of the first aspect of the invention are provided wherein the granules are enclosed inside a sachet. Yet other preferred embodiments of the first aspect of the invention are provided wherein the granules are enclosed inside a capsule.

According to a second aspect of the present invention there is provided a method of producing a pharmaceutical preparation comprising the steps of: producing granules having a predetermined cross-sectional profile and a predetermined axis; sorting the granules into at least one fraction according to their aspect ratio; and selecting for further processing those granules in a given fraction or given fractions. The step of sorting the granules is effected by passing the granules through a length separator.

Such embodiments are able to produce granules which are non-spheronised and which exhibit a more controlled and reproducible dissolution profile, and are thus especially suited to applications where a well defined release after immersion in a solvent is required, such as in oral dose pharmaceuticals.

The granules may form at least 10% by number, 30% by number, 50% by number, 70% by number, 90% by number, or even 100% by number of the pharmaceutically active granules of a single dose of the pharmaceutical preparation.

In preferred embodiments of the second aspect of the invention, the length separator comprises a surface having cavities formed therein, the surface being arranged to follow a predetermined path such that a granule on the surface having a predetermined relationship between the dimensions of a given cavity and the length of the granule will fall and be classified into a given fraction.

Such embodiments are especially effective at rapidly and effectively achieving the required granule distributions on laboratory and production scales. Such embodiments are able also to achieve a continuous, rather than discontinuous, process, and can produce improvements in yield and process time.

Preferred embodiments of the second aspect of the invention are provided wherein the granules are prepared by: passing a homogenised wet mass through an extruding screen having apertures with predetermined dimensions formed therein; and comminuting the extruded mass to form granules.

Such embodiments are convenient to form on production scales and allow well-defined aspect ratios to be determined.

Preferred embodiments of the second aspect of the invention are provided wherein the surface is a cylinder, the predetermined path is rotary about the axis of the cylinder, and a receptacle for collecting the granules to be classified into a given fraction is positioned off-axis of the cylinder.

Such embodiments are able to be applied to large quantities of granules without requiring a large equipment footprint.

In preferred embodiments of the second aspect of the invention the cylinder is arranged to rotate at less than 1 revolution per second. Preferred embodiments of the present invention are provided having an inner diameter of between 10 cm and 200 cm. Particularly preferred embodiments are provided wherein the cylinder is arranged to rotate at peripheral surface speeds of less than 1 m/s.

Such embodiments are able to produce a particularly improved granule aspect ratio distribution, and may also improve the time in which for a certain number of granules a preferred aspect ratio distribution is reached.

In preferred embodiments of the second aspect of the invention, the cavities of the surface are each suitable for hosting a single granule of predetermined dimensions.

Such embodiments are able to particularly effectively extract well-defined fractions of granules.

Preferred embodiments of the second aspect of the invention are provided wherein granules not selected for further processing are further again comminuted and subsequently further again sorted according to their aspect ratio. Particularly preferred embodiments of the second aspect of the invention are provided wherein the granules not selected for further processing are further again sorted in the same process as the sorting of the granules in an earlier step of sorting.

Such embodiments allow a reduction in waste and improvement in usable yield, and in particularly preferred embodiments permit such an improvement in yield without significant increase in apparatus footprint.

According to a third aspect of the present invention, there is provided a use of a length separator in a method for producing a pharmaceutical preparation, wherein the use occurs during selecting granules of which each has a predetermined axis and the same predetermined cross-sectional profile and of which at least a number have an active pharmaceutical ingredient. Preferably, each of the granules has an active pharmaceutical ingredient, and even more preferably, that active pharmaceutical ingredient is the same for each of the granules. The granules are non-spheronised granules. In a preferred embodiment, the method for producing a pharmaceutical preparation comprises applying a coating to selected granules so that the active pharmaceutical ingredient is released with a predetermined rate. Preferably, the length separator comprises a surface having a number of identically preshaped cavities formed therein. Each cavity is suitable for hosting a single granule. The surface is arranged to follow a predetermined path, so that a granule initially kept in a cavity will fall out of the cavity at a position along the predetermined path. That position depends on the length of the respective granule. The use of this particular length separator allows for an efficient and straightforward way of separating granules having a length shorter than a predetermined length. It is possible to set the predetermined length such that the selected granules are no longer likely to fracture up into smaller granules. Accordingly, the amount of total surface area of the granules is stable in that it will not significantly alter during further processing. On that basis it is possible to apply a coating to a large batch of the selected granules, such that a coating has a predetermined thickness and the release rate of the active pharmaceutical ingredient can accurately be controlled.

The selected granules may form at least 10% by number, 30% by number, 50% by number, 70% by number, 90% by number, or even 100% by number of the pharmaceutically active granules of a single dose of the pharmaceutical preparation.

BRIEF DESCRIPTION OF THE DRAWINGS

To better explain the claimed invention, and to show how the same may be carried into effect, reference will now be made, by way of example only, to the accompanying Drawings, the contents of which are described in the following paragraphs.

FIG. 5 shows granule length distributions for:
a) current production; and
b) granules obtained by the cavitied cylinder separator using a cylinder with a cavity size of 2000 µm and tear-drop shaped cavities
(left axis: relative distribution; right axis: cumulative distribution).

FIG. 6b shows a representation of the statistical significance, by means of the "F-test", of the distribution data displayed in FIG. 6a.

DETAILED DESCRIPTION OF THE INVENTION

Figure 1A:
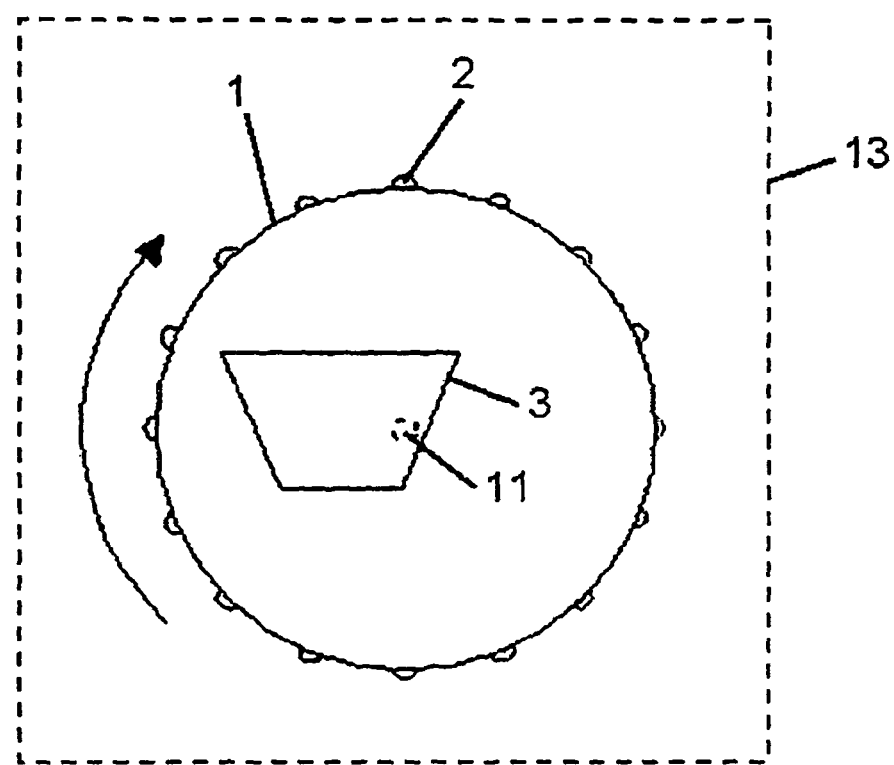
FIG. 1 shows schematic representations of an example of a length separator showing:
a) the working principle (in cross-section);
b) an enlarged section of the separator shown in a); and
c) an example showing a collector, here in the form of a trough comprising an upper stationary part receiving the selected granules and a slightly sloped lower vibrating part conveying the selected granules towards an outlet.

Without wishing to be bound by any particular theory or explanation of the advantages of the present invention, in the making of the present invention it was observed that granules comprising an active pharmaceutical ingredient tend to fragment during the coating process, particularly when the granules have a relatively large aspect ratio. One can easily imagine that a long, rod-shaped granule, having a high aspect ratio, will tend to fragment across the length direction during further processing. Such behaviour is a feature of geometry, and particularly of aspect ratio, provided that the major dimensions of the granule are much larger than the microstructure of the granule. On the other hand, short granules (of aspect ratio less than 1) will tend to abrade on edges and faces during processing to a slightly more spherical configuration. However, such abrasion, also referred to as attrition, is not considered to be a form of spheronisation, as the granules will not reach a stage in which more directions for rolling become available, or in which a dominant predetermined axis and/or cross-section is not recognisable. The granules still have edge-like features.

While some authors define aspect ratio as ratio of longest to shortest dimension, or of shortest to longest dimension, when discussing an extruded granule having a predetermined axis (e.g. the axis of extrusion) and being of defined cross-section (e.g. the extrusion cross-section), it is most useful to define aspect ratio in terms of granule length along its predetermined axis, i.e. the extrusion axis, divided by the smallest cross-sectional dimension (the diameter in the case of particles having a circular cross-section). In the present application, we use this definition since it is the ratio between these dimensions that is considered to have the greatest impact on fracture properties. The present invention, however, has application beyond extruded granules to any similarly-formed granules.

Typically, extruded granules and similarly-formed granules have a recognisable axis, for example an axis of rotational or mirror symmetry, along which the cross-section perpendicular to that axis is substantially similar, barring broken corners or slight variations in the manufacturing process, or even slight tapering of the granule toward one or both ends. This is typically the extrusion axis in extruded granules. In any similar bulk granules, it can also be defined as the axis perpendicular to which the dominant cross-sectional profile is substantially similar to that of the other granules. So, while the granules may individually vary in length along such an axis, they will all exhibit substantially similar cross-sections perpendicular to it.

The term "similarly-formed granules" encompasses granules which have the characteristics of extruded granules in terms of a predetermined axis and an identical predetermined cross-sectional profile, even though these granules are formed by a process that is different from extrusion. A moulding technique could for instance impose a predetermined axis and a predetermined cross-sectional profile onto a long granule, which may after its production, fragment into shorter granules in the same way as extruded granules do.

The term "predetermined axis" may be seen to refer to an axis imposed on a granule to be formed even before the granule is formed. The axis is predetermined in the sense that it is determined by the apparatus used for forming a lengthy fiber-like material prior to its fragmentation into granules. A predetermined axis may thus be defined as an axis imposed onto the granule to be formed before its formation in a granulation process. A mold also imposes an axis onto a granule before the actual formation of the granule.

A similar view may apply to the term "predetermined cross-sectional profile". It is imposed onto the granule before its formation in a granulation process, by the apparatus used for forming a lengthy fiber-like material, which results upon fragmentation of that material into the granules.

It is clear that granules subjected to a spheronisation process are not or no longer granules having a predetermined cross-sectional profile.

It is particularly useful in considering the general teaching of this application to regard granules having a predetermined axis and the same predetermined cross-sectional profile to be granules having a predetermined axis and, perpendicular to that axis, the same predetermined cross-sectional profile at at least three axially separated positions along that axis. Adopting such a definition can achieve the advantages of the invention whilst ensuring that granules with minor deformities and irregularities fall within the scope of the present invention and granules which are substantially spherical or irregular are excluded from the definition.

If the aspect ratio as defined above is large, the granules have rod, prism or cylindrical type geometry, and applied forces are believed to tend to snap the granule at some point along this axis, reducing its length but not substantially affecting its cross-section. On the other hand, if the aspect ratio as defined above is small, applied forces are believed to tend to abrade or crush the granule, altering its cross-section. If the aspect ratio as defined above is close to or less than one, the probability of applied forces fracturing the granule along this axis is believed to become low or minimal, and abrasion and crushing may become the dominant fracture mode.

Accordingly, a definition of aspect ratio as given above is considered to be both very useful for characterising the present invention and understanding its behaviour, and is also entirely consistent with aspect ratios less than 1, which are, in other less useful definitions of aspect ratio, not defined. When the length is longer than the largest of the cross-sectional dimensions, however, this definition of aspect ratio becomes identical to the alternative definition as largest dimension divided by smallest dimension.

On the one hand, fragmentation of granules during coating increases the overall surface to be coated. Hence, if a certain amount of coating liquid, calculated for achieving a specific coating thickness, is used, the resultant coating thickness is reduced. On the other hand, if the fragmentation of granules occurs towards the end of the coating process, the newly generated granule surfaces tend to receive only a small amount of coating or no coating, so that the overall dissolution properties of the granules will deviate from that for which the amount of coating liquid was calculated. Moreover, the dissolution profile is likely to become faster and less well-defined, in that some of the granules will dissolve well in advance of others, as those granules having received a lower amount of coating on a freshly generated surface will dissolve more rapidly. Such granules, in oral dosage forms, may release their active ingredient undesirably early, e.g. in the stomach rather than the intestine. As a result, it was concluded that it is preferable to exclude granules exceeding a certain length from the coating process in order to accomplish a more uniform coating of the granules.

Therefore, there is a need in the art for granules having well-defined length distributions, and particularly granules whose length distribution strongly disfavours granules having an aspect ratio such that they fragment during further processing, including coating. There is also a corresponding need for methods and apparatus to separate granules for pharmaceutical compositions according to their length so that a well-defined length distribution of granules, and therefore a well-defined dissolution and release profile for active ingredients, may be obtained.

Embodiments of the present invention are of use in the pharmaceutical field for producing granules comprising a desired active pharmaceutical ingredient or even a combination of several active ingredients.

The granules used as starting material for the present invention suitably have a common cross-sectional profile. The three-dimensional shape may be cylindrical, ellipsoidal, or any other shape desired, for example a triangular, rectangular or other polygonal prism. In the presently preferred embodiments of the invention the shape is cylindrical, i.e. the diameter of each granule is along its length essentially identical to the diameter of any of the other granules. Thus, only the length dimension varies. However, the present invention is also applicable to mixtures having a variety of profile geometries in the granules, for example a mixture of circular and hexagonal prismatic granules.

The granules are suitably produced by extrusion. The extruder comprises a screen, which has numerous holes with a diameter of between 0.6 and 1.8 mm, preferably 0.9 mm. The thickness of the screen is between 0.9 and 2.0 mm; preferably, the thickness of the screen is 1.5 mm. The holes are arranged with a geometry which imparts the desired cross-sectional profile to the extruded granules, for example circular holes for producing cylindrical granules, or triangular holes for triangular prismatic granules. Each hole can have the same cross-section through the screen or be tapered in either direction, compared to any of the other holes. Preferably, the holes are tapered, each hole having a cross-section at the inlet side of the screen that is larger than the cross-section at the outlet side of the screen, the preferred outlet diameter is 0.9 mm and the preferred inlet diameter is 0.95 mm.

After the extrusion, the granules may be dried in a suitable device. Advantageously, the drying device is a fluid bed. However, other possibilities known by the skilled person may also be used, such as oven drying, irradiation with e.g. infrared, ultraviolet or microwaves, and freeze-drying.

If a fluid bed is used, it may be designed in such a way that the dwelling time in the fluid bed is approximately 2 hours. However, shorter or longer times are also contemplated, depending on the dimensions and composition of the granules.

In some cases the fluid bed is separated in two parts. In the first part the granules are dried on the surface to avoid their sticking together. In this part a random mixing of the granules takes place. In the second part of the fluid bed the final drying takes place and the granules are guided through the fluid bed by a suitable pattern of holes in the bottom plate of the fluid bed.

When the granules are dry they are discharged from the fluid bed and may be transferred to a mill to reduce the length of the granules. The milling process is preferably conducted with a conical mill, however other milling types may be used, such as bead mills, jet mills, blenders, or manual comminution. The milling may generate a small amount of fines that may be removed by sieving before the granules are ready for treatment in accordance with the present invention. However, the present invention is also realisable without milling.

The wet mass employed in the production of the granules used in the present invention may be prepared by any suitable process depending among other factors on the specific active pharmaceutical ingredient and the pharmaceutical formulation. The exact composition of the wet mass will determine the parameters of the extrusion and optional drying step; selection of suitable parameters is well within the capacity of those skilled in the art.

It is also conceivable that the wet mass, as extruded into fiber-like material, is chopped into shorter fragments of such fibers, to influence or even fix the length of the majority of the granules produced in this way. This may result in a more uniform length distribution, with a well-defined narrow peak. The selection of granules having a required length distribution may then be applied as a form of quality control.

To arrive at granules being an embodiment of the claimed invention, a method of selecting granules having the required length distribution is thus in any case preferably employed.

One embodiment of such a method uses a length separator to sort the granules, which comprises a surface provided with a number of pre-shaped cavities, each suitable for hosting one of the granules. Such a surface may be termed a cavitied surface. The surface is arranged to follow a predetermined path so that from each cavity a granule hosted therein will fall out at a drop-out position along the path. Each drop-out position is determined by the longest dimension of the granule hosted in the respective cavity.

The length separator further comprises a collector for collecting granules from at least one predetermined drop-out position. An embodiment of such a length separator comprises a rotatable cylinder having an essentially horizontally oriented axis provided on the interior surface with a number of cavities, for instance an array of cavities.

The term "essentially horizontally" also comprises embodiments in which the rotating cylinder is slightly inclined, e.g. the cylinder may be inclined 1-15 degrees, suitably 2 to 6 degrees, relative to the horizontal position. The inclination is typically in the direction of an outlet, such that the particles treated in the length separator are assisted by gravity in the movement from the inlet towards the outlet. In other arrangements, the reverse arrangement is possible, with the outlet end higher than the inlet end, to maximise dwell time in the separator.

Although this embodiment of a length separator is very practical, other embodiments are possible. It is for instance possible that the surface provided with the pre-shaped cavities is part of a conveyor belt and/or that the cavities are provided at an exterior surface of a cylinder. The principles of operation of other equivalent arrangements, and how they are to be configured in an effective manner, will be clear to the skilled person from the present description.

Figure 1B:
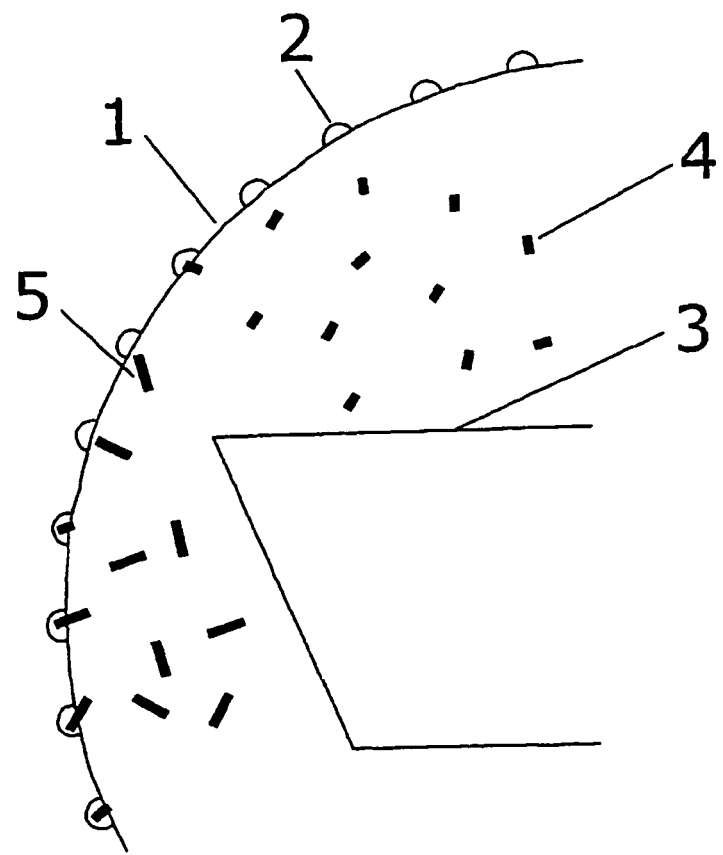

FIG. 1a discloses a schematic drawing of an exemplary length separator 13. The length separator 13 comprises a cylinder or mantle 1 internally provided with cavities 2, preferably in the entire circumference thereof. The arrow depicts the direction of the rotation. Inside the cylinder 1, a trough 3 is provided, as at least part of a collector. When the cylinder is rotated granules below a certain cut-off value will be discharged in the trough. FIG. 1b shows a detail of the apparatus shown in FIG. 1a. The granule 4 is of a length below a certain cut-off value and is therefore received by the trough 3, while the length of granule 5 is above the cut-off value and therefore remains in the cavitied cylinder.

The cavities in the interior surface of the cylinder are provided in an array. The cavities may be provided in a pattern or randomly and the cavities are usually substantially evenly distributed. Suitably, cavities are provided in essentially the entire circumference of the cylinder. For an efficient separation, cavities are provided along essentially the entire length of the cylinder, such as at least 60%, preferably at least 70% and most preferably at least 85% of the length.

The shape of the cavities may be any geometrical form, such as cylindrical, teardrop shaped, hemispherical, box shaped, polyhedral, etc. In a certain embodiment, the cavities are cylindrical, such that the centre axes of the cavity cylinders are directed towards the rotational axis of the rotating cylinder. In preferred embodiments, asymmetrical or "teardrop" cavities may be provided. In such a "tear-drop" part of the cavity, the leading part of the cavity with respect to the direction of movement of the cavity, is relatively shallow. The trailing part of the cavity is relatively deep, the deeper part of the cavity being in the trailing part of the cavity.

In some configurations, different cylindrical portions of the cylinder, being relatively displaced axially lengthwise, may have differently constructed and/or dimensioned cavities in order to extract various length fractions; combinations of different cavities at any particular axial portion are also contemplated, depending on the selection criteria. The cavities may be prepared by various methods providing the desired geometrical shape. Thus, the cavities may be prepared by embossing, milling, drilling etc. of a surface. The cavities may be indents, in which case the surface may be referred to as an indented surface.

The surface which is provided with the number of pre-shaped cavities is preferably a stainless steel. This has the advantage that the surface can be cleaned up and prepared to a standard required for use of the surface within the pharmaceutical industry. Furthermore, the cavities can be formed by local deformation of the surface; forming the cavities by embossing (or deep drawing) in a stainless steel cylinder is possible. Such cavities exhibit a particular benefit when granules of an active pharmaceutical ingredients are treated with a length separator having such a surface, that as the cavities have a smooth surface without edges (as opposed to cavities formed by, e.g., drilling), the granules rarely get stuck in the cavities and are therefore less prone to breakage.

The geometrical shape of the cavities depends on the desired separation profile, and thus the distribution of granule lengths to be obtained. In one configuration, wherein the surface provided with a number of pre-shaped cavities is part of a cylinder, the cavities have parallel to the surface a longest dimension ranging from 0.5 to 3 mm. In the event a cavity is cylindrical, this longest dimension corresponds to the diameter. In a preferred configuration, the diameter is between 1 to 3 mm, more preferred 1.5 to 2.5 mm. The diameter is an important parameter in determination of the so-called cut-off value, i.e. the value at which larger particles are excluded. In one configuration, the cavity is tapered along a direction into which the surface will follow the predetermined path. The latter configuration is particularly suitable for preventing granules from being blocked in the cavity. Other variables which may be adjusted to optimise the effectiveness of the cavities include depth or cavity and steepness of the cavity bending edges.

The length separator is advantageously operated at conditions where centrifugal forces exerted on the particulate matter are not significant compared to the gravitational force. A centrifugal acceleration may be calculated from $\omega^2 r$, where $\omega$ denotes the rate of rotation (in $s^{-2}$) and r the radius of the predetermined path, or in an advantageous embodiment of the length separator (in m). The acceleration may be compared directly to the gravitational acceleration, g, which is of the value 9.81 m/s$^2$. Thus, for a length separator of 400 mm diameter rotating at approximately 30 rpm the centrifugal acceleration exerted on granules in the cylinder will be around 0.05 m/s$^2$, considerably smaller than the acceleration due to gravity.

In configurations in which the surface of the length separator provided with cavities is cylindrical, the diameter of the cylinder is typically between 10 cm to 100 cm. The diameter may be larger in certain embodiments, for example those in which granules of lower density are processed. Generally, however, the diameter is selected in the range of to 90 cm, suitably 40 to 70 cm, to obtain a desired productivity in terms of amount of granules (kg) treated per hour. The length of the cylinder may be selected in accordance with the desired capacity. In general, the length is between 10 cm and 200 cm, suitably 100 to 200 cm and preferably 130 to 160 cm. A typical relationship between length and diameter is from 0.5:1 to 5:1; in presently preferred configurations, from 1:1 to 3:1. In a particularly presently preferred configuration the diameter is about 60 cm and the length of the separator is about 150 cm.

For a configuration where a rotatable cylindrical surface is provided with cavities, the rate of rotation is generally selected so as to obtain a sufficient productivity. Generally, the rate of rotation is selected together with the diameter to obtain a centrifugal acceleration below ½ g, preferably below $\frac{1}{10}$ g, more preferred below $\frac{1}{100}$ g. In a certain configuration, the diameter of the essentially horizontally rotating cylinder is 10 cm to 200 cm and the rotational speed may be selected in the range of 10 to 100 rpm (revolutions per minute), preferably 20 to 50 rpm, and most preferably 25 to 40 rpm.

The granules discharged from the cavities when the essentially horizontally-oriented cylinder is rotated may be recovered by any suitable means. In one embodiment, the length separator comprises, as a collector, a trough located in the cylinder, said trough being capable of receiving granules discharged at a predetermined drop-out position, i.e. at a certain elevation of the cavities in which the granules have been accommodated. Generally, the trough extends over the entire length of the length separator. Positioning the trough off-axis of the cylinder may be particularly suitable for collecting a particular length distribution; the position and dimensions of the trough may be adjusted easily by those skilled in the art to tune the distribution obtained.

Following collection, the selected granules may then be conveyed to an outlet for further treatment. In one embodiment of the invention, the granules are transported in a chute after they have been recovered in the trough. The chute is connected to the outlet. The chute may be slightly sloped and/or vibrating to assist the selected granules in the movement towards the outlet. The chute may be a part of the trough or may be provided separately. In some embodiments, the trough comprises an upper stationary part receiving the selected granules and a slightly sloped lower vibrating part conveying the selected granules towards an outlet. The separation of the upper stationary and the lower vibrating part provides for easy servicing of the apparatus. Other means for transportation of the selected granules may include a screw conveyor.

Figure 1C:
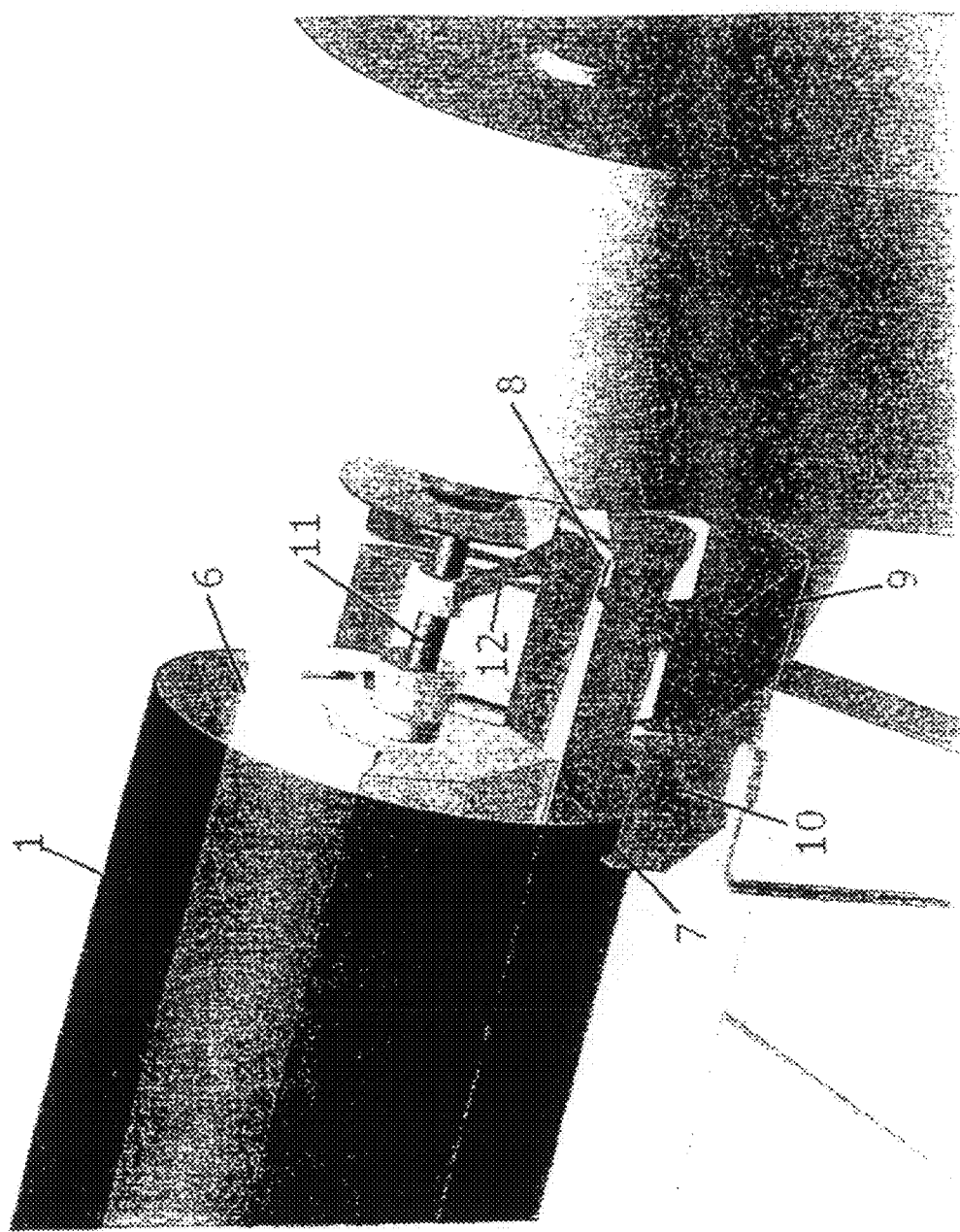

FIG. 1c shows a view of a particular length separator such as may be usable in one embodiment of the method of the present invention. The length separator comprises a rotatable cylinder 1, at the interior surface provided with cavities.

The cylinder 1 is rotated at a constant speed by an electric motor (not shown). In the cylinder a trough is positioned. The trough consists of an upper stationary trough 6 for receiving the selected granules and a slightly sloped lower vibrating conveyor 7. The selected granules (termed the in-size fraction) are conveyed in the lower vibrating conveyor 7 of the trough towards an exit 8. The granules discharged from the exit 8 are received by a transporter 9. The particles received by transporter 9 are transported to a storage container (not shown). The remaining granules in the rotating cylinder (termed the oversize fraction) are discharged to a transporter 10 and conveyed to a storage container.

The upper stationary trough 6 of the trough is mounted on a rotatable axle 11, using bearings. The lower vibrating conveyor 7 of the trough is vibrated in axial direction by the rotation of a disc provided with buttons. The lower trough 6 of the trough is flexibly mounted on the axle 11 through a plate spring 12 for holding the vibrating conveyor.

The oversize fraction may be recycled for a further treatment in the length separator. The recycling step may include that the longer particles are comminuted by milling and returned for renewed treatment in accordance with step b). The granules for recycling may be milled by a conical mill or similar means.

The granules being embodiments of the present invention and being obtainable by embodiments of the method of the invention generally have a narrower granule length distribution than those obtainable by mere sieving of equivalent starting granular material. Granule size distributions, and the descriptive statistics thereof, are determined in accordance with the "Determination of Granule Length Distribution" as set out in below "Example 2". Such a method is applicable to both coated and uncoated particles.

During any of the processing steps from granulation to selecting granules, small fines may be produced by a process of friction related attrition. This, however, does not alter the overall shape of the granules and is certainly not a form of spheronisation.

The selected granules may be used for the preparation of a pharmaceutical composition. According to preferred embodiments of the present invention the selection step is followed by a step of applying onto the selected granules a pharmaceutically acceptable coating material.

Further to the active pharmaceutical ingredient, the granules may contain one or more pharmaceutically acceptable binders or fillers or a mixture thereof. Suitable binders include acacia, gelatin, hydroxypropyl cellulose, hydroxypropylmethyl cellulose, methyl cellulose, polyethylene glycol (PEG), povidone, sucrose, starch or a mixture of any of these. Povidone (polyvinyl pyrrolidone, PVP) is a preferred binder. Binders may be used in a total amount of 1 to 10, or 2 to 8, or 3 to 7, or 4 to 6, or 5% by weight of the granules. Suitable fillers include inter alia microcrystalline cellulose. Fillers may be used in a total amount of 10 to 70, or 20 to 60, or 40 to 50, or 50% by weight of the granules.

Both binders and fillers as well as possible further excipients are well known to a person skilled in the art and can be selected in a routine manner.

The granules may be coated in any coating device applicable to the process. The skilled person will readily know which devices would be suitable for the present process, such as for example a fluid bed system, e.g. a Kugel coater. In some embodiments, the coating material is applied to the selected granules as a solution, and coating of the selected granules is provided upon evaporation of the solvent. The granules are preferably coated with a polymer dissolved in a suitable solvent for the polymer, preferably an organic solvent such as acetone. As the granules selected for coating are unlikely to further fragment into shorter granules, it is possible to use a coater in which the forces exerted on the granules are relatively high, so that the coating can occur within a relatively short space of time.

In order to be able to determine the amount of polymer that has to be applied to the granules, the surface area is measured, or known on the basis of earlier measurements carried out for granules produced and selected in the same way.

Any type of measurement is in principle suitable. However, usually the measurement will be based on image analysis of a representative and statistically relevant sample of the selected granules. The image analysis will further be referred to below. Based on a known correlation between the amount of polymer per surface area and the dissolution rate profile, the amount of polymer needed can be predicted from the determined surface area of the granules.

The selected coating polymer inter alia depends on the desired release pattern, e.g., delayed release or extended release. Release-modifying coating agents which extend the release of the active-pharmaceutical ingredient include ethyl cellulose, carnauba wax, shellac or a mixture thereof. Enteric or delayed release coating agents include polymethacrylate, commercially available in the form of Eudragits, e.g. Eudragit L 100 or Eudragit NE 40 D. When an extended release pattern is desired, ethyl cellulose is the most preferred coating agent.

From an article published in 1988 in "Drug Development and Industrial Pharmacy", 14(15-17), 2285-2297, by G. Ragnarsson and M. O. Johansson, it is known that smaller granules (i.e. granules with a large surface area per volume) would for a given thickness of the coating, provide a larger release rate than larger granules (i.e. granules with a smaller surface area per volume) would demonstrate for the same thickness of coating. In other words, if the smaller granules should have the same release rate as the larger granules, then the coating applied to the smaller granules should be thicker so that the release rate can be the same for each of these particles. This highlights the importance of a very uniform granule size distribution, in particular a narrow aspect ratio distribution where granules are cylinder-like and have the same cross-sectional profile and dimension. On the basis of this article and insights presented in the International Journal of Pharmaceutics, 63 (1990) 189-199, an article by M. Eriksson, C. Nyström and G. Alderborn, both incorporated herein by reference, a person skilled in the art will be able to establish how much coating is needed for a given surface area to obtain a certain release rate. Hence, if the number of those granules are known and the aspect ratio distribution is known, then the correct amount of thickness can easily be calculated. If needed, routine experiments can verify the correctness of the parameters applied. In less optimal situations, it is also a task which lies within the standard skills of a developer in this field to find suitable corrective measures for establishing the optimal amount of coating.

The granule size distribution of the coated granules of the present embodiment of the invention is similar to that of the uncoated granules obtainable by the method of the present invention, as the coating thickness does not have a substantive influence on the length of the granules, and the granules have been selected to avoid the occurrence of significant fragmentation in the coating process.

The granule size distribution, or the granules aspect ratio distribution, can be obtained on the basis of microscopy combined with image analysis, for instance as described by Cynthia S. Randall in Chapter 6, Particle Size Distribution, of the book titled "Physical Characterisation of Pharmaceutical Solids" edited by Harry G. Brittain, 1995.

In a preferred embodiment, suitable for the treatment of inflammatory bowel disease, the active pharmaceutical ingredient is 5-aminosalicylic acid (5-ASA) or any salt or ester thereof. The salts of 5-ASA may be acid addition salts, in particular the hydrochloride, but any pharmaceutically acceptable, non-toxic organic or inorganic acid may be used. 5-aminosalicylic acid is also known by synonyms including mesalazine, 5-aminosalicylic acid, 2-hydroxy-5-aminobenzoic acid; 3-carboxy-4-hydroxyaniline, 5-asa, mesalamine, rowasa and 5-amino-2-hydroxybenzoic acid, and has the molecular formula $C_7H_7NO_3$ and a molecular weight of 153.14. It is registered under Cas registry number 89-57-6 and Einecs 201-919-1.

Also salts formed with the carboxylic acid group may also be used. As examples alkali metal salts (K, Na), or alkaline earth metal salts (Ca, Mg) may be mentioned; however, any pharmaceutically acceptable, non-toxic salt may be used. The Na and Ca salts are preferred.

Applicable esters include e.g. straight chain or branched $C_1$-$C_{18}$ alkyl esters, e.g. methyl, ethyl, propyl, isopropyl, butyl, isobutyl, amyl, hexyl, heptyl, octyl, nonyl, decyl, lauryl, myristyl, cetyl, and stearyl, etc., straight chain or branched $C_2$-$C_{18}$ alkenyl esters, e.g. vinyl, allyl, undecenyl, oleyl, linolenyl, etc., $C_3$-$C_8$ cycloalkyl esters, e.g. cyclopropyl, cyclobutyl, cyclopentyl, cyclohexyl, cycloheptyl and cyclooctyl, etc., aryl esters, e.g. phenyl, toluoyl, xylyl, naphthyl, etc., alicyclic esters, e.g. menthyl, etc., or aralkyl esters, e.g. benzyl, phenethyl, etc.

Generally, the selection of the active ingredient depends on the selected type of, formulation, the disease pattern, especially the site and type of the disease, and the desired release of the active ingredient.

The physical state and solubility characteristics of the 5-ASA derivatives must be taken into account when selecting a suitable carrier composition for the ingredient. The preferred active pharmaceutical ingredient at present is the free acid, 5-aminosalicylic acid.

The effective oral dose depends on the extent of the disease and for adults usually amounts to 0.5-1.0 g four times a day, or alternatively 2.0-4.0 g once daily. Generally about 20 mg/kg body weight of 5-ASA or a salt or ester thereof (calculated as 5-ASA) will be the recommended initial daily dosage subject to adjustment in accordance with the observed results of the treatment.

At present, the preferred release pattern is a continuous release following arrival in the small intestine. This release was originally designed so as to enable the pharmaceutical composition, e.g. Pentasa®, to be effective against both Crohn's disease and ulcerative colitis.

However, in case it should be desirable to secure an early release in the small intestine (in the case of Crohn's disease) or a delayed release until arrival in the colon (in the case of ulcerative colitis), the release pattern can be controlled by varying different parameters of the coating. The skilled person will be able to readily determine how such release conditions may be achieved; nonetheless, for the sake of completeness the skilled person may find the disclosure of WO 81/02671, which is hereby incorporated by reference, of some benefit in achieving a particular release profile.

In a certain presently preferred method, the granules comprise 5-ASA. Thus, the granules may be prepared by wet mixing of 5-ASA with a solution of a binder, such as polyvinylpyrrolidone (PVP, Povidone) in water (e.g. 21.3% w/w). Specifically, 5-ASA and an aqueous solution of PVP are mixed and added to the extruder. Alternatively, 5-ASA and the aqueous solution of PVP may be mixed in the extruder. In either case, the wet mass consisting of 5-ASA and PVP is extruded through a screen and allowed to fall into the device for drying of the wet granules.

The aqueous solvent is preferably water of a suitable quality, but may contain additives, such as chelating agents, antioxidants, reducing agents, buffers and pH adjusting agents.

The granules comprising 5-ASA as the active pharmaceutical ingredient may specifically be prepared as described in, e.g., WO 97/23199, WO 03/032952 or WO 2004/093884, incorporated herein by reference. In one particular embodiment, the granules contain prior to coating 5-ASA and binder only, as described in WO 2004/093884.

In certain aspects the present method is utilised for the preparation of prolonged release tablets, sachets or capsules useful for the treatment of ulcerative colitis or Crohn's disease. In one embodiment, the coating material is a cellulose derivative, such as ethyl cellulose. In some tablet embodiments, the excipients comprise a tablet carrier, such as microcrystalline cellulose, a lubricant, such as magnesium stearate and optionally further excipients such as talc.

In the below disclosure, including Examples, we will demonstrate how pharmaceutical preparations being embodiments of the present invention and comprising the advantageous granules of the present invention have improved properties compared with those having granules not falling within the scope of the claims Comparative Example A Production of Granules for Tablets Comprising 5-ASA (Water Based Granulation Process)

The manufacturing process for 5-ASA tablets can be divided into a number of steps: preparation of granulation liquid; mixing of 5-ASA with water and PVP; extrusion; fluid bed drying; milling; sieving; coating; sieving again, purging, dry blending with excipients, and compression to tablets Step 1: For one batch of granulation liquid 118.4 kg of water was filled into a Müller drum. The mixer was put into position and started. 32 kg of PVP was slowly sprinkled onto the water and the mixer was allowed to run a fixed time until all PVP was dissolved.

Step 2 and 3: 640 kg of 5-ASA was placed in a vibrating Prodima hopper and by the use of a conveyor the 5-ASA was transported up to a weight belt feeder dosing the 5-ASA into a continuous production line. In the first part of the production line the 5-ASA and the water solution of PVP were mixed to a wet mass before being transported into the extruder. After extrusion of the wet mass of 5-ASA and PVP/water through a screen mesh 0.9 mm, the granules fell directly into the fluid bed dryer.

Step 4: The fluid bed dryer was divided into two main sections. In the first section, the granules were dried on the surface to prevent them from sticking together. In this section of the fluid bed, a random mixing of the granules took place. After a certain residence time, the granules were moved into the second part of the dryer where the actual drying took place. In the second part of the dryer the granules were guided by the use of the drying air through the dryer.

When the granules were dry they were allowed to fall into a drum placed under the fluid bed. The fluid bed was constructed in such a way that the overall dwelling time in the fluid bed was approximately 2M hours.

Step 5: The drums containing the dry granules were placed upside down on top of the mill and the granules were gently milled using a screen. After passing the mill, the granules were allowed to fall into a drum.

Step 6: The granules were sieved using a Mogensen vibration sieve with screen dimension 0.8 mm. Granules which passed the screen were discarded.

Step 7: 200 kg of sieved granules were coated in a Kugel coater, being a fluid bed system, with a coating liquid consisting of ethylcellulose dissolved in acetone.

In order to be able to determine the right amount of polymer necessary to apply on the granules to get the desirable dissolution rate profile, the surface area of the granules was measured prior to the coating process. The prediction of the quantity of polymer that was necessary to apply on the granules has been developed based on the fact that there is a correlation between the amount of polymer per surface area and the dissolution rate of the granules. Once the surface area characteristics for a given granulation size distribution is known, the calculated quantity of polymer may be repeatedly used on comparable batches of granules. After finishing the coating process, the coated granules were loaded into a drum for further processing.

Step 8: After the coating process, the coated granules were sieved in a Prodima rotation sieve. Large lumps were discarded.

Step 9: After sieving, the batch of coated granules was divided into two drums for purging with compressed air or nitrogen. The granules were purged for 6-14 hours, although shorter times, such as 30 minutes, are also considered reasonable in practice. This purging process was necessary to reduce the amount of residual solvent (acetone) in the coated granules.

Step 10: 178.56 kg coated Pentasa granules were weighed out and loaded into the Prodima blender together with 69.34 kg microcrystalline cellulose. After mixing for 210 seconds the blender was stopped. 0.335 kg magnesium stearate and 3.02 kg talc were added to the blend and the ingredients were mixed for 90 seconds. The blend gave approximately 335,000 tablets.

After mixing the blend was discharged into Muller drums ready for compression.

Step 11: The final blend of coated granules and excipients was compressed on a rotary tabletting machine. Weight of each of the tablets: 750 mg. Dedusting of the tablets was performed as an in-line process with the tabletting machine. After dedusting the tablets were loaded into bulk containers holding approximately 30,000 tablets each.

Comparative Example B

Preparation of 5-ASA Granules for Sachets

A batch for the production of 180,000 sachets of prolonged release granules was provided as outlined below, using the quantities indicated in Table 1.

TABLE 1

Ingredients for 5-ASA granules for sachets.

| Constituents | Quantity | Specification |
|---|---|---|
| 5-ASA | 180 kg | Ferring |
| PVP | 9 kg | Ph. Eur. † |
| Water, purified | 33.3 kg * | Ph. Eur. † |
| Ethyl cellulose | 1.9 kg ** | Ph. Eur. † |
| Acetone | 188 kg * | Ph. Eur. † |

\* Evaporates during production.
\*\* The amount of ethylcellulose was adjusted to ensure the desired dissolution profile of the finished product.
† Ph. Eur. refers to the current edition of the European Pharmacopeia at the time of filing of the present application.

The manufacturing method followed closely the manufacturing method described in Example A, with some modifications. In particular, no tablets were made, so no dry blending with excipients was performed (Step 10) and no tabletting performed (Step 11). Also, the amount of ethylcellulose is reduced as there is no compaction to a tablet, and thus a reduction in the amount of coating applied is needed to obtain the desired dissolution profile.

The manufacturing process for the formulation can be divided into a number of steps: preparation of granulation liquid; granulation of 5-ASA with water and PVP; extrusion; fluid bed drying; milling; sieving; coating; sieving; and purging.

Thus, the process for the manufacture of granules for sachets differs from the tablet process in step 7 as explained below, and steps 10 and 11 of Example A were not included.

Step 7: When the coating step was performed and followed by production scale sieving acceptable release characteristics were achieved. After finishing the coating process, the coated granules were loaded into a drum for further processing.

This batch provided granules with the composition listed in Table 2.

TABLE 2

| Composition of granules for sachets | |
| --- | --- |
| 5-ASA | 94.3% by weight |
| PVP | 4.7% by weight |
| Ethylcellulose | 1.0% by weight |

Example 1

Demonstration of Classification of Granules by Cavitied Cylinder Separator

Two batches of uncoated granules of 5-ASA were produced according to comparative Example A (i.e. the product of Step 6), and these granules were applied to a laboratory scale cavitied cylinder length separator.

The separator had a rotatable cylinder having a diameter of 400 mm and a length of 500 mm; the inclination of the cylinder was fixed at 4° and the rotational speed of the rotating cylinder was 32 rpm. The cylinder was provided with a steel mantle embossed with tear-drop shaped cavities. In other words, the cavities had the shape of half-spheres or half teardrops as cross-sectioned along their axes. The cavity is oriented with its axis along the direction of the predetermined path which the surface is arranged to follow; in this case the axis is oriented along the tangential direction of the cylinder.

Figure 2:
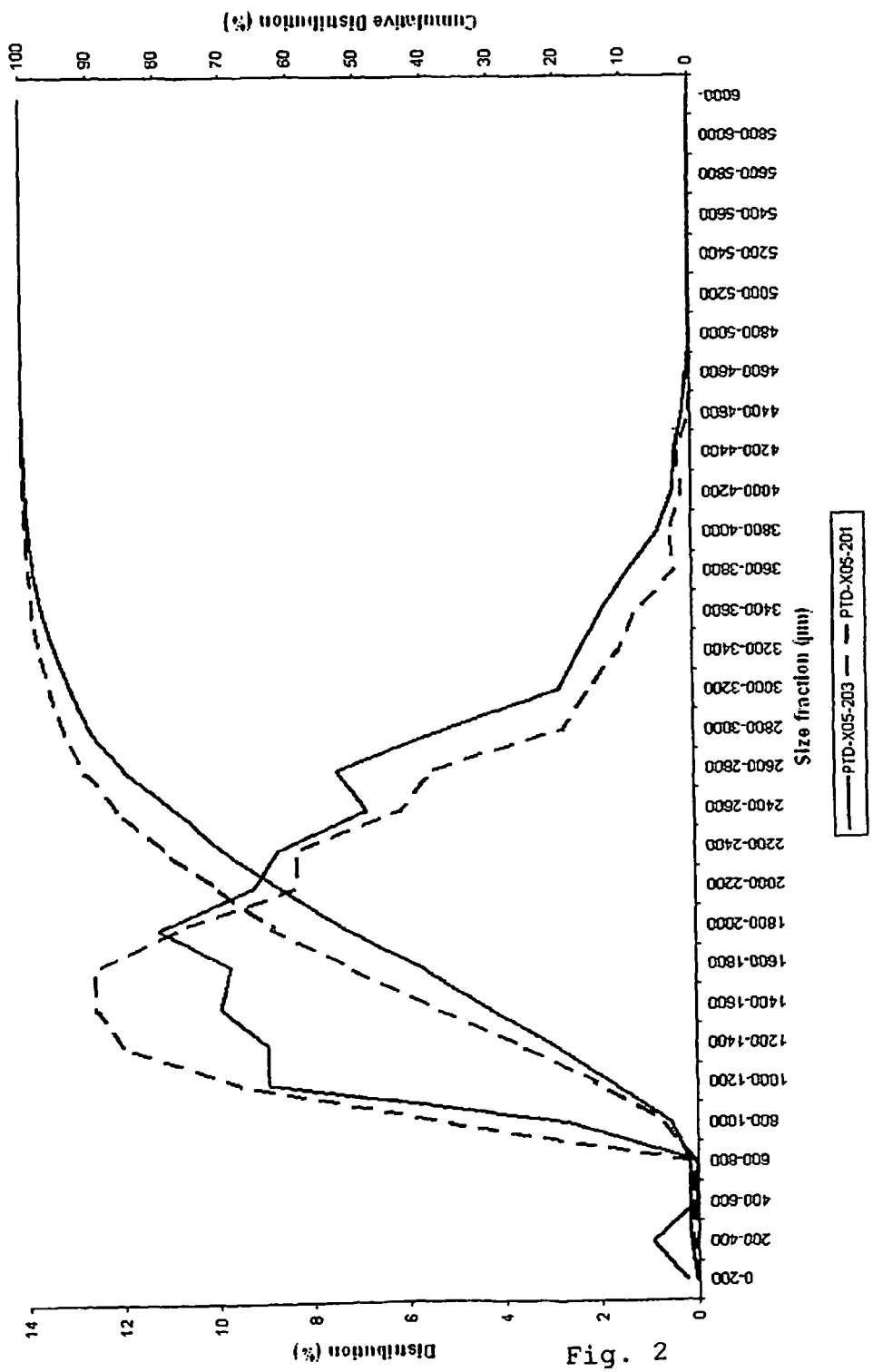
FIG. 2 discloses granule length distributions by count of two batches of uncoated 5-ASA granules according to the measurement protocol given below (left axis: relative distribution; right axis: cumulative distribution).
Figure 3A:
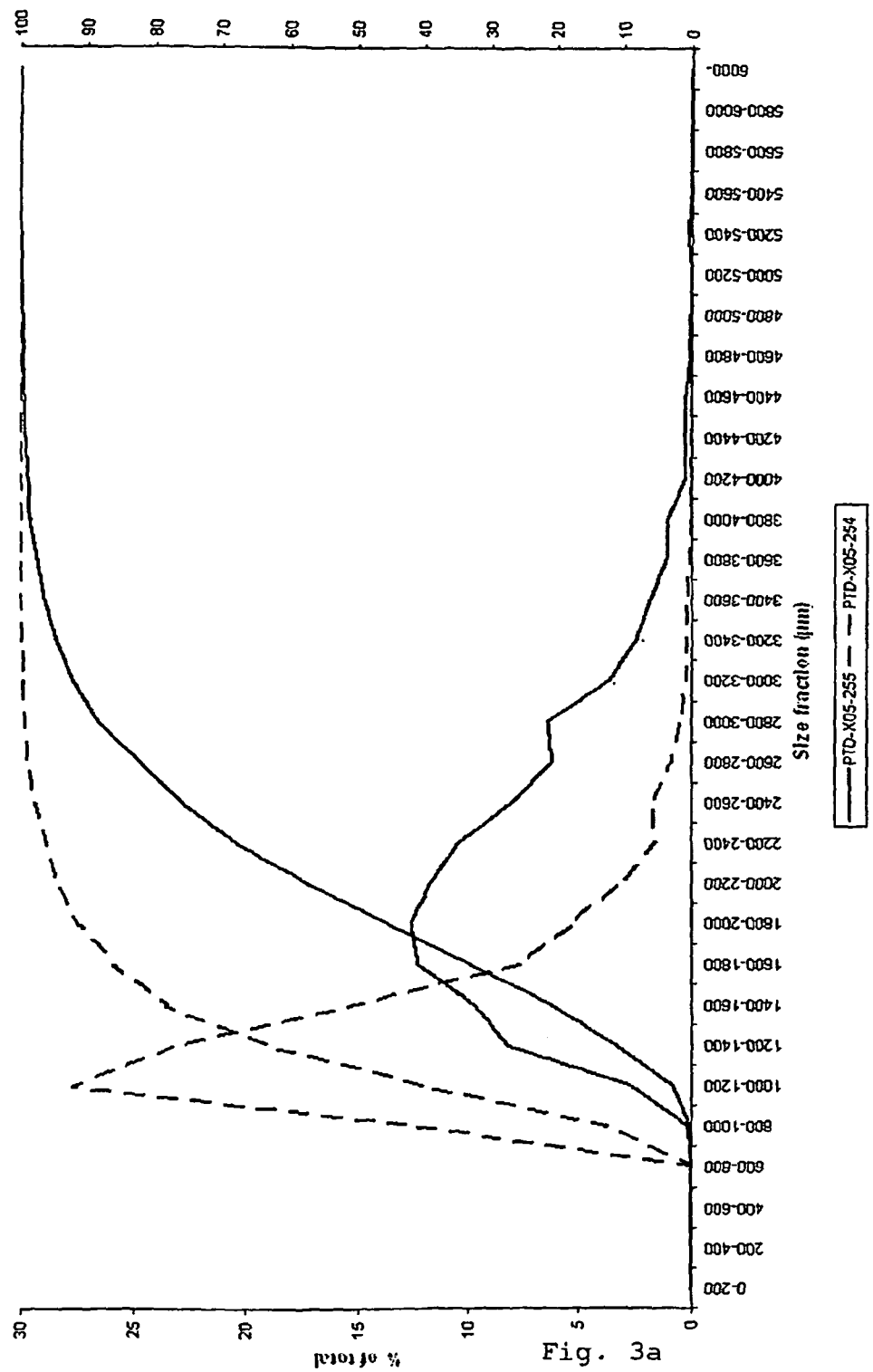
FIG. 3 illustrates granule length distributions of 5-ASA granules separated in a cavitied cylinder separator with cylinders with cavities of:
a) 1500 µm diameter (PTD-X05-255=cylinder fraction; PTD-X05-254=trough fraction);
b) 1750 µm diameter (PTD-X05-257=cylinder fraction; PTD-X05-256=trough fraction); and
c) 2000 µm diameter (PTD-X05-259=cylinder fraction; PTD-X05-258=trough fraction), respectively (left axis: relative distribution; right axis: cumulative distribution).
Figure 3B:
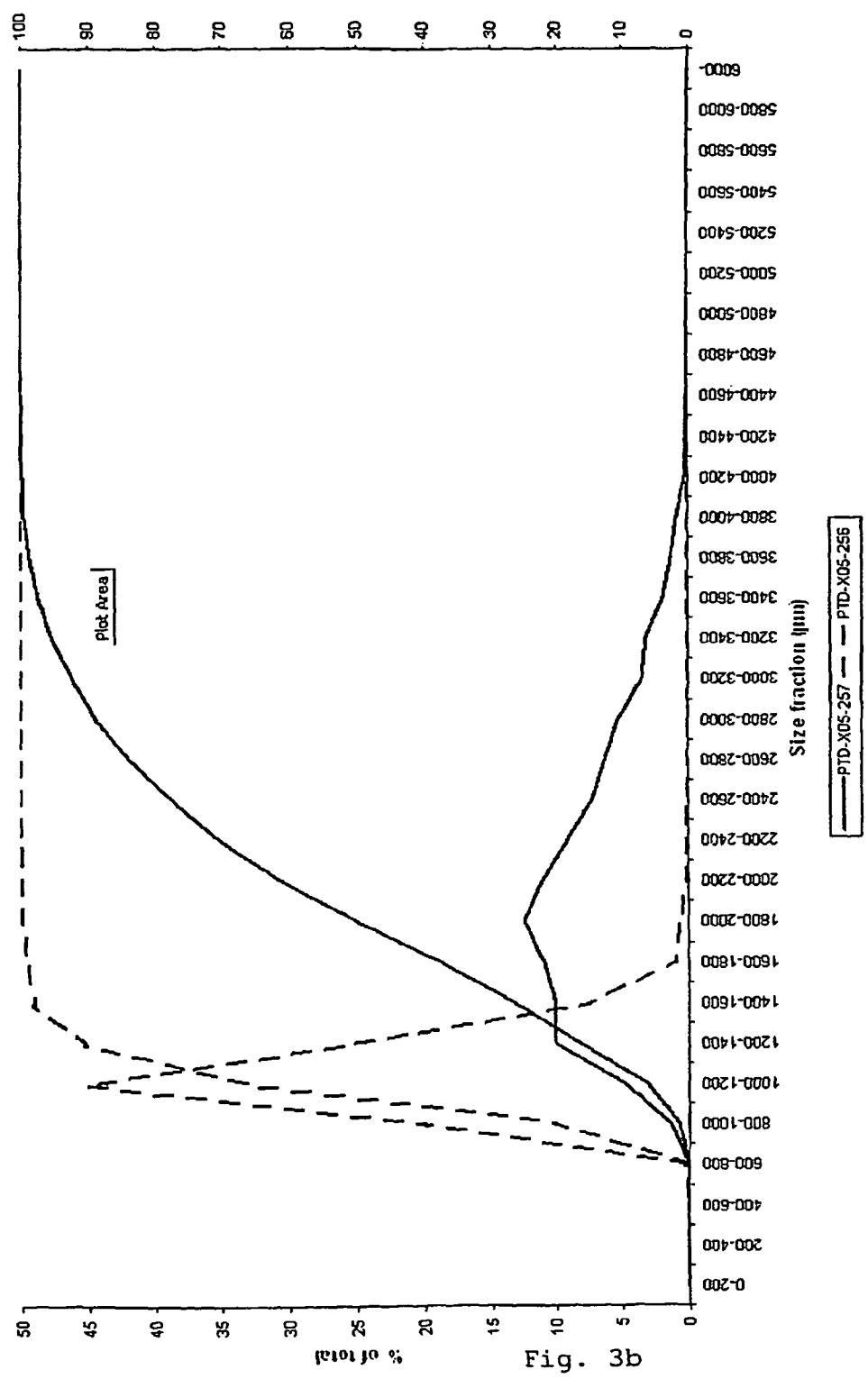
Figure 3C:
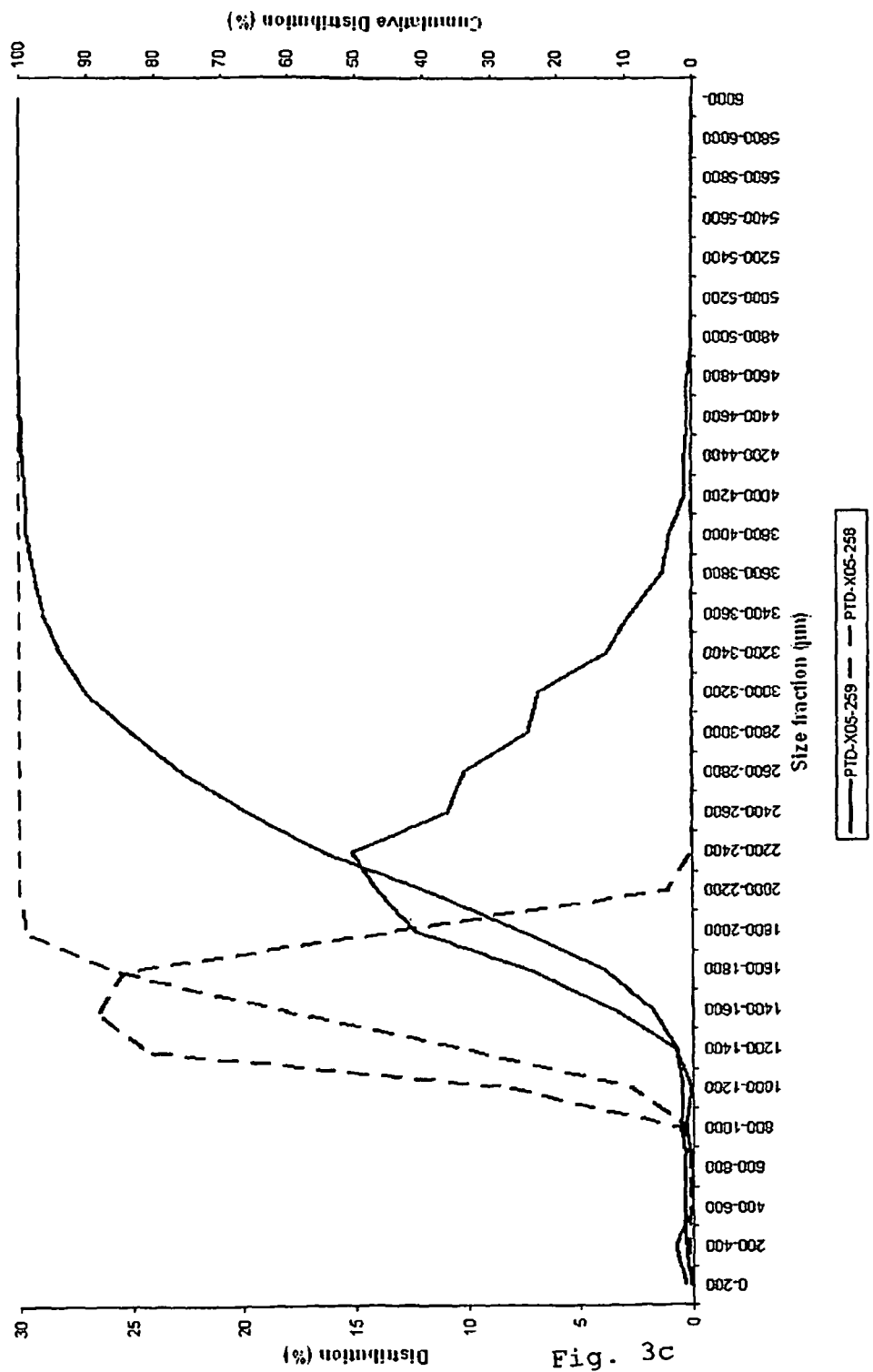
Figure 4A:
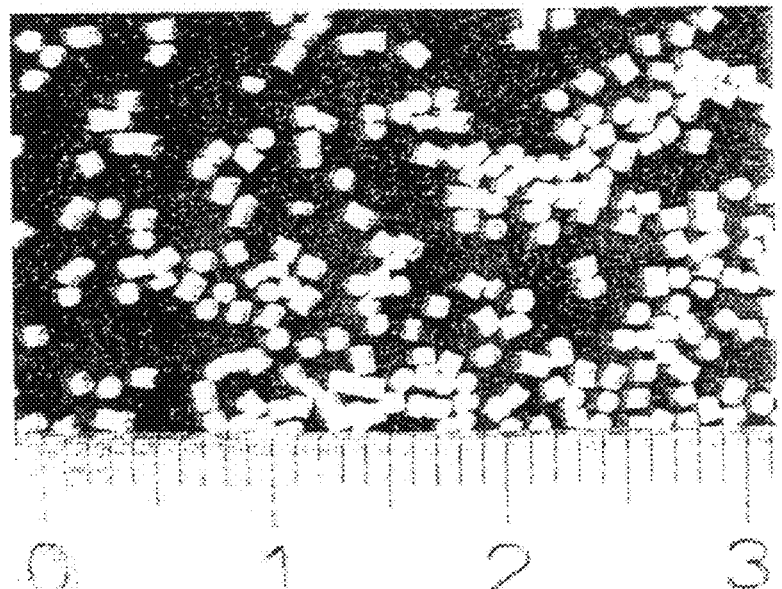
FIG. 4 shows photographs of granules sorted using a cavitied cylinder separator where (a) is the trough fraction and (b) the rotating cylinder fraction.
Figure 4B:
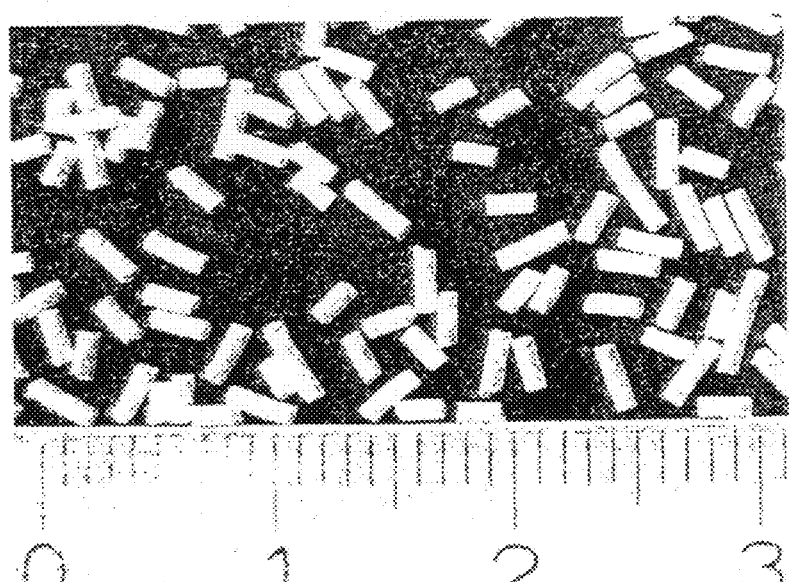

Initially, granules from one batch were applied to the cavitied cylinder separator furnished with cavities of 1500 μms, 1750 μms or 2000 μms diameter, respectively. The length distribution of the starting material was similar to that shown in FIG. 2, and the results of the classification experiments are shown in FIGS. 3a to 3c showing the length distributions of the trough and the rotating cylinder fractions. Examples of granules obtained in the trough and the rotating cylinder fractions are depicted in FIGS. 4a and 4b respectively.

Therefore, it is demonstrated that such a method is capable of discriminating long granules from shorter granules, and that the distribution of lengths, and thus aspect ratios, obtainable from this method is sharply defined.

Example 2

Determination of Granule Length Distribution

The Granule Length Distribution can be determined by any suitable method. Although each method may have its own shortcomings, it is usually possible to correct for these, so that a suitably accurate result can be obtained. In general it will be possible to verify the outcome by a manual assessment of the length of each granule, using for instance microscopy. This would then also provide the corrective measure to improve the accuracy of the method employed. A convenient, accurate and more automatic determination is based on image analysis.

The median length and the amount of granules >2000 μm may be determined by using a method of image analysis, distributing the granules on a presentation plate by vibration. This method was selected for the present example. The equipment used was a fully automated image analysis equipment, known by the trade name of VideometerLabXY. The measurements were performed by backlight using a 1600×1200 pixel black and white camera with a pixel size of 0.024 mm. The lens used on the camera was a multispectral lens with a magnification of 1. The presentation plate had a size of 23×29 cm and the granule density was approximately 12 granules/cm². The sample measured was approximately 8000 granules.

The image analysis was performed by scanning the presentation in a raster manner with an overlap between the individual images of 500 μm. The images were analysed individually, overlapping granules were excluded and duplicate granules already detected in a previous image were neglected. A Hough circle transformation filter was used to detect and exclude standing granules. The entire presentation plate was covered by 10×10 images. The software determined the length of a granule by a bounding box principle, not using a principal axis measure since this provides statistically "noisy" results due to a substantially rectangular shape of the granules.

Of course, in certain embodiments in which a particularly large number of granules have aspect ratio close to or less than 1, a significantly higher proportion of granules will be found in measurement to be standing on end and will thus be excluded by the Hough circle filter. The skilled person will recognise such results, and will understand that in such cases, the measured aspect ratio distribution, determined by the above method, will exclude such granules from the count and the distribution. Nevertheless, even in such cases the benefits of having the measured aspect ratio distribution as defined in the claimed invention will apply, as those particles of aspect ratio close to 1 are considered to be statistically far less likely to suffer undesirable fracture events during coating. In such cases, the skilled person will still recognise such an embodiment as lying within the scope of the present invention, even if a significant proportion of granules have been excluded from the measurement. In many cases encountered in practice, however, the proportion of granules so excluded is generally expected to be small, and thus not to significantly affect the measured distribution.

It is also possible that extra effort is made to obtain the length of each of the granules, thus also those standing on one end. For instance a method of tracing these in the image and manipulating these for "manual" assessment of the length, using microscopy, is not inconceivable. Obtaining a correction value that can then be applied to the more automatically formed data is envisageable. A fully manually carried out assessment of the length of each granule will of course allow for a very accurate determination of the length distribution, respectively aspect ratio distribution.

The following data was measured on every granule and presented in an output file: bounding box length; bounding box width; area; ferret diameter, max; ferret diameter, min; theoretical surface area; theoretical volume.

The data generated in summary for the entire sample was: median of bounding box length; D10 of bounding box length; D90 of bounding box length; span of bounding box length; theoretical specific surface area; count percentage>2000 μm; number of particles analysed.

Ferret diameter was calculated based on an angular resolution of 5 and all values are given in mm with a resolution of 0.01 mm.

Span is calculated as (D90−D10)/D50, where D90 and D10 are the $90^{th}$ and $10^{th}$ percentiles of the distribution, respectively, and D50 is the median.

Derivable from any of the bounding box length values and distributions are corresponding aspect ratio values and distributions, obtainable by dividing the bounding box length by the extruded granule diameter.

The granule length characteristics of the materials obtained using the three different rotating cylinders as set out in Example 1 and measured by the method of the present Example are summarised in Table 4. In each case, the granules were passed once through the cavitied cylinder separator.

All given data, values and summary statistics unless otherwise stated refer to number or count of granules rather than, for example, values per unit mass or per unit volume.

TABLE 4

Granule characteristics of selected granules.

| Batch | Fraction | Cavity size (μm) | Median length (μm) | Span | % > 2000 μm | % < 2000 μm |
|---|---|---|---|---|---|---|
| 1 | Trough | 1500 | 1264 | 0.76 | 8.5 | |
|   | Cylinder | 1500 | 2079 | 0.81 | | 45.6 |
| 1 | Trough | 1750 | 1136 | 0.38 | 0.3 | |
|   | Cylinder | 1750 | 2008 | 0.89 | | 49.8 |
| 1 | Trough | 2000 | 1530 | 0.42 | 1.18 | |
|   | Cylinder | 2000 | 2342 | 0.63 | | 25 |

Two different batches were then each passed through the cavitied cylinder for 5 consecutive cycles, i.e. after each cycle of classification the cylinder fraction was passed through the cavitied cylinder separator again and the trough fractions weighed and eventually pooled. A cylinder with 2000 μm-diameter tear-drop shaped cavities was used in this process. The results are summarised in Table 5.

TABLE 5

Granule characteristics of selected granules.

| Batch | Fraction | Cavity size (μm) | Median length (μm) | Span | % > 2000 μm | % < 2000 μm |
|---|---|---|---|---|---|---|
| 1 | Trough | 2000 | 1530 | 0.42 | 1.2 | |
|   | Cylinder | 2000 | 2517 | 0.50 | | 7.6 |
| 2 | Trough | 2000 | 1484 | 0.54 | 2.7 | |
|   | Cylinder | 2000 | 2426 | 0.49 | | 6.7 |

For batch 2, 17.5 kg of starting material was applied to the cavitied cylinder separator, and the results achieved by weighing each fraction from each cycle of the 5-cycle process are summarised in Table 6.

TABLE 6

Removed fractions of 5-ASA granules in 5 consecutive cycles of separation in a cavitied cylinder separator equipped with a cylinder with 2000 μm diameter tear-drop shaped cavities.

| Run no. | Weight (g) | Percentage | Cumulative percentage |
|---|---|---|---|
| 1. | 2970 | 24 | 24 |
| 2. | 1200 | 9.7 | 33.6 |
| 3. | 375 | 3 | 36.7 |
| 4. | 260 | 2.1 | 38.8 |
| 5. | 110 | 0.9 | 39.6 |

The specific surface areas of each of the two fractions of granules were measured after 5 cycles through the separator with the cylinder with 2000 μm diameter tear-drop shaped cavities and compared to corresponding values for the starting materials. The results are presented in Table 7.

TABLE 7

Specific surface areas of 5-ASA granules before and after classification by 5 cycles through a cavitied cylinder separator equipped with a cylinder with 2000 μm tear-drop shaped diameter cavities.

| Batch | Fraction | Specific surface area ($cm^2/g$) |
|---|---|---|
| 1 | Starting material | 63.4 |
|   | Trough | 65.5 |
|   | Cylinder | 61.0 |
| 2 | Starting material | 63.1 |
|   | Trough | 63.5 |
|   | Cylinder | 62.4 |

The classification experiments performed showed that the cavitied cylinder separator was capable of producing an in-size fraction with a median granule length of ~1500 μm and a span of ~0.5. This is by far superior to the sieving technique which produced granules with a median length of 1800-2000 μm and a span of ~0.8. The cavitied cylinder separator was thus able to produce a fraction of granules with a smaller median length and a much more narrow size distribution. Furthermore, the specific surface area obtained by fractionating granules in the cavities cylinder separator showed a higher specific surface area for the trough (in-size) fraction than for the cylinder fraction.

Example 3

Influence of Parameter Values on Cavitied Cylinder Separator Classification Process To further describe the influence on different operating parameters on the outcome of the cavitied cylinder separator classification, another set of experiments was performed using a batch of uncoated 5-ASA granules (produced according to comparative Example A). The cavitied cylinder separator was equipped with a cylinder with 2000 μm-diameter tear-drop shaped cavities, and the granulate was classified in 3 consecutive cycles conducted as described in Example 1. During the experiments different values for the feed rate and the rotational speed were tested. The results obtained by weighing the different fractions are summarised in Table 8.

TABLE 8

Mean and relative standard deviation of final measurements. The last column is the fraction/percentage removed of the 42.3% w/w available

| Settings | | Mean | RSD | % of the |
|---|---|---|---|---|
| RPM | Feed rate (kg) | (%) | (%) | available |
| 36 | 56 | 38.3 | 0.9 | 90.5 |
| 25 | 56 | 38.2 | 1.9 | 89.8 |
| 36 | 3 | 30.3 | 0.7 | 71.4 |
| 25 | 3 | 40 | 1.8 | 94.6 |

From Table 8 it can be seen that the output was influenced by the rotational speed of the cylinder at a low feed rate, while the output observed at a high feed rate was unaffected by the rotational speed of the cylinder.

The granule length distribution of experiments performed at high feed rates and different rotational speeds were determined to evaluate if the output of the cavitied cylinder was consistent regardless of the rotational speed of the cylinder. The length distributions of the resulting granules were determined by image analysis as per Example 3 and are summarised in Table 9.

TABLE 9

Granule length characteristics of the starting material and trough fractions

| Settings | | Median, | | Percentage larger |
|---|---|---|---|---|
| RPM | Feed rate (kg) | length (μm) | Span | than 2000 μm (by weight) |
| Starting material | | 1869 | 0.98 | 57.7 |
| 36 | 56 | 1468 | 0.57 | 3.9 |
| 25 | 56 | 1409 | 0.58 | 2.6 |

The overall conclusion on the capacity and efficiency is that regardless of the feed rate and rotational speed the cavitied cylinder was capable of extracting ~90% of the granules available in the size range desired. The granule length distribution of the trough fraction was in the size range desired.

Example 4

The effect of the sorting method on coating

Breakage of the granules during the coating step may be problematic due to difficulties arising in predicting the dissolution profile of the coated granules. This is relevant for both manufacturing processes described in comparative Examples A and B. In order to examine how the method of the present invention affects the subsequent coating procedure in comparison to the method of comparative Example A, a set of experiments was set up.

A batch of granules was prepared as described in comparative Example A, and the length distributions before and after coating were measured. Uncoated granules from the batch were classified in a cavitied cylinder separator and then coated as described in comparative Example A. The cavitied cylinder separator employed in the experiment contained an array of tear-drop shaped cavities of 2000 μm size. Length distributions of uncoated granules classified by treatment with the cavitied cylinder separator and of the length sorted granules after coating were measured. The results of the length distribution measurements are shown in FIG. 5.

Figure 5A:
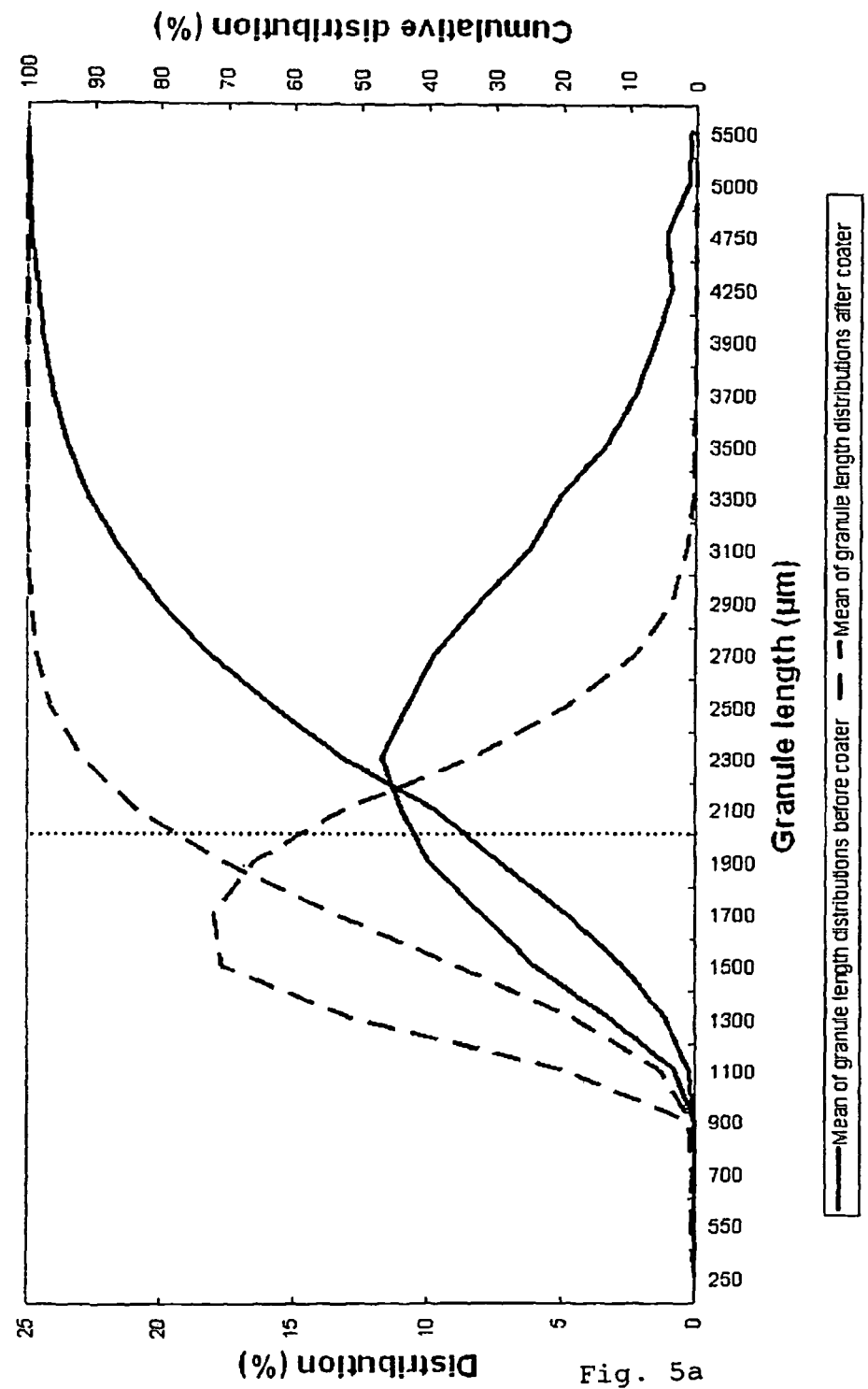
In FIG. 5a, full lines represent granule length distributions before the coater; dashed lines represent granule length distributions after coating.
Figure 5B:
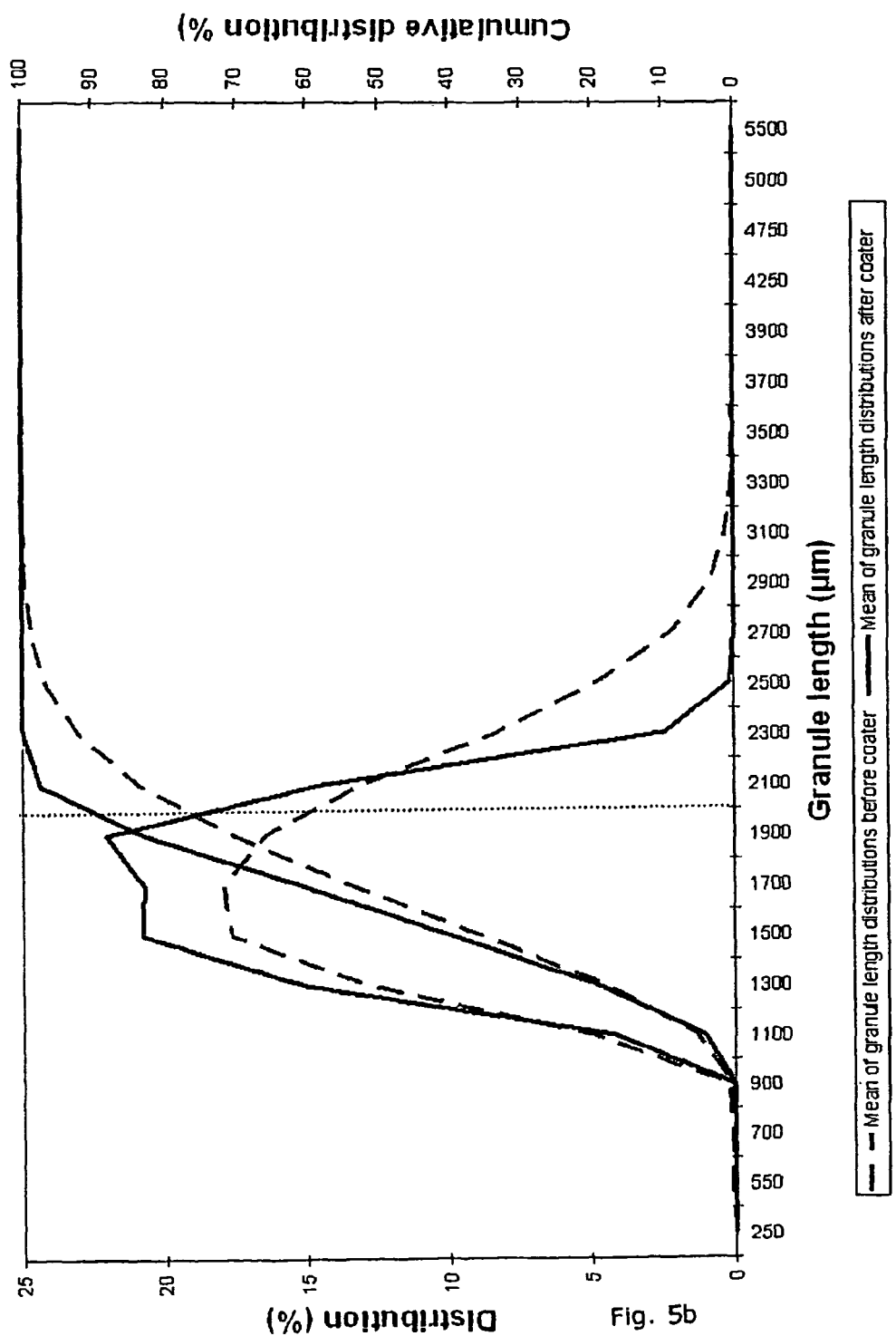
In FIG. 5b, dashed lines represent granule length distributions before the coater; full lines represent granule length distributions after coating. The dotted vertical line indicates the exemplary desired maximum size of the granules, 2000 µm).

From FIG. 5a it is seen that the range of the granule length distribution was narrowed from 645-4900 μm to 600-2500 μm by the coating process of the current method. This shows that long granules were broken during the coating process. The median length was reduced from 1954 μm (RSD 7.3%) to 1441 μm (RSD 4.5%). The result of this breakage was an unpredictable outcome of the coating process. In contrast, the granules produced using the method of the present invention do not suffer from this drawback as seen in FIG. 5b. These results are considered to hold for any granule having a microstructure much smaller than the granule diameter, and particularly for granules of pharmaceutical preparations having a diameter of between 0.25 mm and 2.5 mm.

Example 5

In-Vitro Dissolution of Coated 5-ASA Granules

This example investigates the effect of the cavitied cylinder separator classification of 5-ASA granules on the variation of their dissolution behavior. Thus, the variation in dissolution of cavitied cylinder separator classified granules for a sachet ("PENTASA 95% sachet granules") is compared with that of unclassified granules for a tablet ("PENTASA tablet granules"). The classified granules, prior to coating, had a median aspect ratio of 1.4 and span of 0.6.

Tablet granules are generally coated with an excess of coating (ethylcellulose) compared to the sachet granules in order to compensate for the effect of the subsequent compression step. For comparing the dissolution of the coated, dried and sieved tablet granules with the sachet granules, samples of the tablet granules are withdrawn during the spraying phase, after an amount of coating has been applied that corresponds to the coating amount applied on the sachet granules. The data sets are therefore directly comparable in all relevant factors.

Ten samples of (unclassified) coated PENTASA tablet granules were withdrawn from routine production batches. Eight samples of classified and coated PENTASA 95% sachet granules were withdrawn from test and validation batches. Following an in-house test protocol, the in-vitro degree of dissolution of each of the samples was determined as a function of time. Data analysis was carried out with the Minitab 15.1.1.0 software, developed by Minitab Inc., USA.

The 90 minutes dissolution results and the respective statistics are summarized in Table 9 below.

TABLE 9

Statistics for the dissolution (90 minutes) of coated PENTASA 95% sachet and PENTASA tablet granule batches for samples withdrawn during the spray phase at a coating factor of $2.0 \cdot 10^{-4}$.

| Type | n | Mean dissolution | Variance | S.D. | R.S.D. |
|---|---|---|---|---|---|
| PENTASA 95% sachet | 8 | 34.1% | 19.0 | 4.4% | 12.9% |
| PENTASA tablet granules | 10 | 40.1% | 157.0 | 12.5% | 31.2% |

S.D. = standard deviation; R.S.D. = relative standard deviation

At 12.5%, the standard deviation of the dissolution of comparative PENTASA tablet granules is 2.8 times larger than that of PENTASA 95% sachet granules obtained in accordance with the present invention (4.4%). Moreover, the variance (spread) of the dissolution results for the inventive product is much more narrow (19.0) than for the comparative, unclassified product (157.0).

Figure 6A:
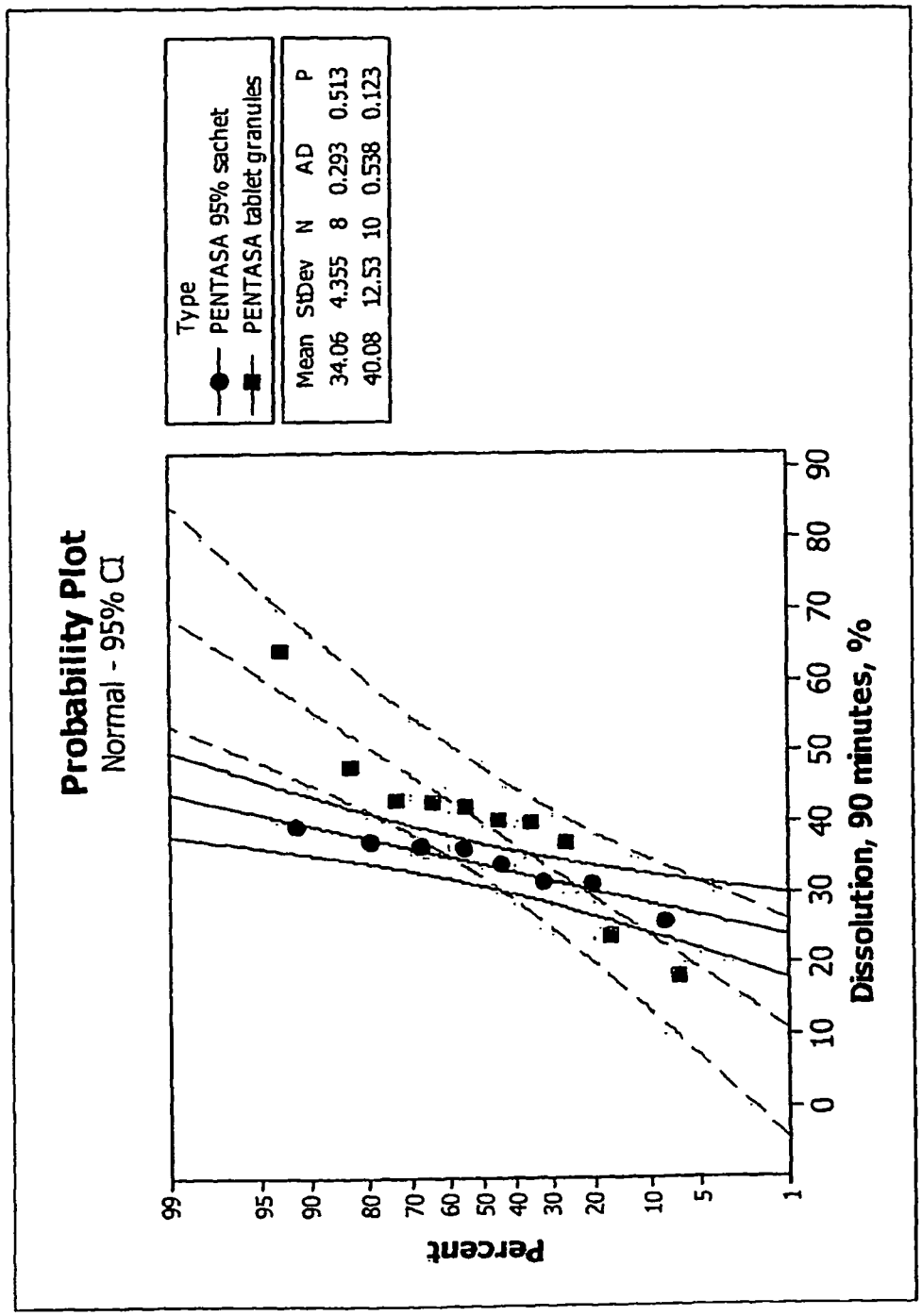
FIG. 6a is a probability plot comparing the distribution of the dissolution data at 90 minutes of a comparative sample of coated granules ("PENTASA tablet granules") and a sample of classified and coated granules prepared in accordance with the present invention ("PENTASA 95% sachet").

For the PENTASA 95% sachet and PENTASA tablet granule samples, the distributions of the dissolution results are not significantly different from normal distributions (see FIG. 6a). Thus, the Anderson-Darling test for correspondence of the distributions with a normal distribution gives p=0.32 for PENTASA 95% sachet and p=0.12 for PENTASA tablet granules.

Figure 6B:
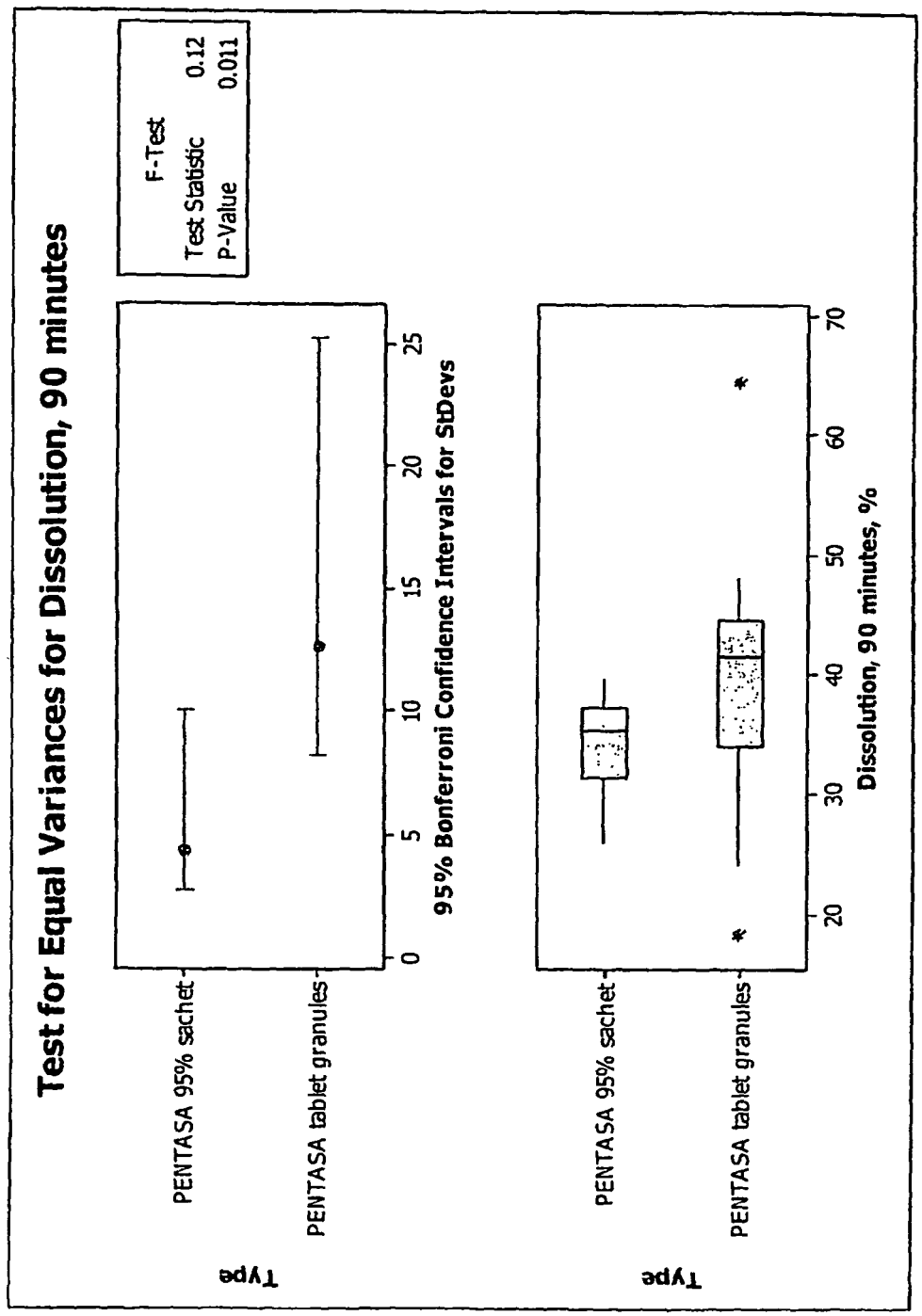

Since the dissolution results suggest a normal distribution (see FIG. 6a), the variations in dissolution of PENTASA 95% sachet and tablet granules can be compared using an F-test. The F-test demonstrates that the variation in dissolution of coated PENTASA 95% sachet granules is significantly lower than the variation in dissolution of coated PENTASA tablet granules (p=0.01) (FIG. 6b).

Figure 7:
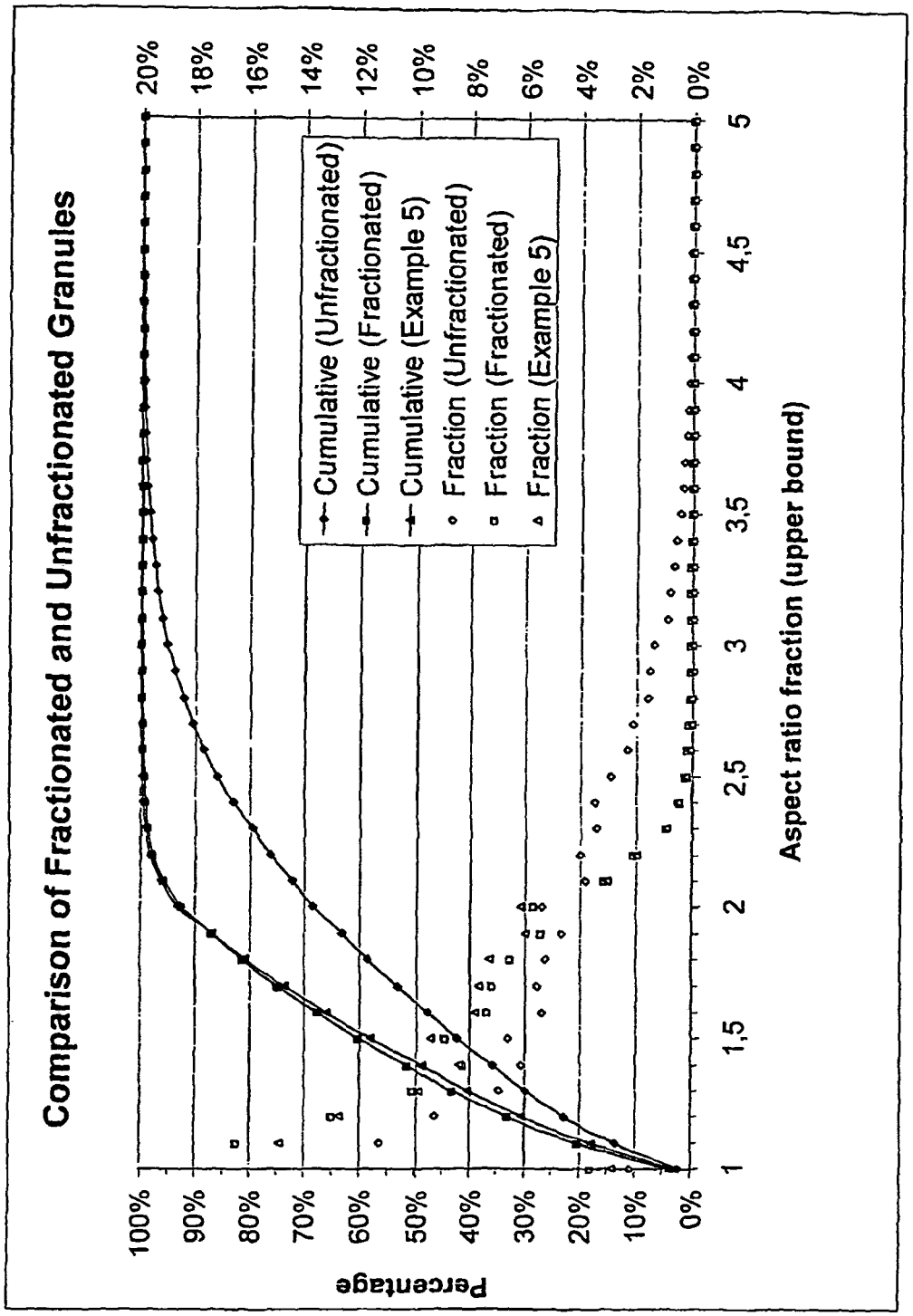
FIG. 7 shows the aspect ratio distribution of a sample of fractionated and unfractionated granules of PENTASA compositions, together with comparative data for the granules of Example 5.

Having further optimised the process for manufacturing scale, six batches of uncoated PENTASA sachet granules (fractionated) and eight batches of uncoated PENTASA tablet granules (unfractionated, sieved) prepared in a comparable manner to those set out above in the instant Example were analysed for length distribution as set out in Example 2. Aspect ratio distributions were calculated based on the length distributions with length having been divided by the extruded diameter of the granules (0.8 mm). The results are shown graphically in FIG. 7, and the statistics pertaining thereto are summarised in Table 10, the data of Example 5 being included for comparative purposes also. It is evident from these figures that the distribution of unfractionated (sieved) tablet granules is more sharply peaked with a considerably smaller tail extending beyond the median value.

TABLE 10

Statistics for the aspect ratio distribution of uncoated PENTASA sachet and PENTASA tablet granule batches.

| Aspect ratio statistic | PENTASA sachet (fractionated) | Example 5 granules (fractionated) | PENTASA tablet (unfractionated) |
|---|---|---|---|
| D10 | 1.1 | 1.1 | 1.1 |
| Median/D50 | 1.4 | 1.4 | 1.7 |
| Span | 0.6 | 0.6 | 0.9 |
| D90 | 2 | 2 | 2.7 |

A reduction in such a tail contributes to the advantageous properties of granules being embodiments of the present invention. Of course, a smaller improvement is observed with a smaller reduction in the tail. Accordingly, the characteristic values set out above represent the preferred embodiment.

However, as noted in the Summary of the Invention, and as set out in the appended claims, granule distributions which exhibit any sharply peaked distribution and reduced tail are also of value, and exhibit some improvement in the dissolution properties over and above the dissolution properties of granules not falling within the scope of the claimed invention. It will be within the ambit of the skilled person to vary the parameters of the selection method used to arrive at a pharmaceutical preparation falling within the claimed scope. The skilled person will also undoubtedly be able to arrive at the claimed pharmaceutical preparations with a variety of selection methods. However, it is the granules themselves having the required distribution properties which are considered to impart many of the benefits of the invention, regardless of how they are produced and selected.

Particularly, embodiments wherein at least 80% by number of the granules, preferably 85%, most preferably 90% have an aspect ratio less than 2.2, preferably less than 2.1, most preferably less than 2 are considered to exhibit degrees of improvement in the dissolution properties of the pharmaceutical preparation through the reduction in the tail above the median. In some cases, it may be desired to narrow the distribution further, and embodiments wherein 80%, 85% or even 90% of granules have aspect ratio less than 1.9, 1.7, 1.5 or 1.2 may also be preferred.

Similarly, embodiments wherein at least 80% by number of the granules, preferably 90%, most preferably 95% have an aspect ratio greater than 0.7, preferably greater than 0.9, most preferably greater than 1.0 are also considered to exhibit improvements in the dissolution properties of the pharmaceutical preparation through reduction in the tail below the median.

The percentages referred to above include percentages within a range of plus/minus 10%. At least 80% is therefore also considered to include 70%. Embodiments wherein the granules have a median aspect ratio below 1.7, preferably below 1.6, most preferably below 1.5 are also considered to exhibit improvements in the dissolution properties of the pharmaceutical preparation through improvements in the centring of the distribution around a preferred value. In some cases, it may be desired to bring the median aspect ratio as close to 1 as possible, and so embodiments having a median aspect ratio below 1.4, 1.3, 1.2 or 1.1 will also be preferred.

And yet, embodiments wherein the granules have a span of the aspect ratio less than 0.9, preferably less than 0.8, most preferably less than 0.7 are also considered to exhibit improvements in the dissolution properties of the pharmaceutical preparation through improvements in the central sharpness of the distribution. Similarly, if it is preferred to bring the median aspect ratio particularly close to 1, it may also be very useful to apply the techniques of the present invention to produce embodiments having span of the aspect ratio lower than 0.5, lower than 0.4 or even lower than 0.3.

In cases where the pharmaceutical preparation is provided in sachets, the amount of granules per sachet can be about 2 grams, corresponding to about 2000 granules. However, also other amounts may be suitable for oral dosage.

All such embodiments can be realised in methods as disclosed above, with suitable parameter choices which are well within the ambit of the skilled person.

The invention claimed is:

1. A composition comprising uncoated, non-spherical, extruded granules, wherein said granules comprise an active pharmaceutical ingredient and have a length along an axis of extrusion and a cross-sectional dimension of extrusion, wherein at least 80% by number of said granules have an aspect ratio of said length to said cross-sectional dimension of greater than 0.7 and less than 2.2.

2. The composition of claim 1, wherein the granules have a median aspect ratio above 1.1 and below 1.7.

3. The composition of claim 1, wherein said granules have a span of aspect ratio less than 0.9.

4. The composition of claim 1, wherein said cross-sectional dimension of extrusion is between 0.25 mm and 2.5 mm.

5. A pharmaceutical composition comprising non-spherical extruded granules comprising an active pharmaceutical ingredient and having a length along an axis of extrusion and a cross-sectional dimension of extrusion, prepared by applying a pharmaceutically acceptable coating to uncoated, non-spherical extruded granules selected such that at least 80% by number of said granules have an aspect ratio of said length to said cross-sectional dimension of greater than 0.7 and less than 2.2.

6. The pharmaceutical composition of claim 5, wherein the coating controls the release of the active pharmaceutical ingredient.

7. The composition of claim 1, wherein the active pharmaceutical ingredient comprises an anti-inflammatory ingredient.

8. The composition of claim 1, wherein the active pharmaceutical ingredient is 5-aminosalicylic acid.

9. A method of producing a pharmaceutical preparation comprising the steps of:
   producing uncoated, non-spherical, extruded granules comprising an active pharmaceutical ingredient and having a length along an axis of extrusion and a cross-sectional dimension of extrusion;
   sorting the granules into at least one fraction according to their aspect ratio of said length to said cross-sectional dimension; and
   selecting for further processing those granules in a given fraction or given fractions having an aspect ratio greater than 0.7 and less than 2.2,
   wherein the step of sorting the granules is effected by passing the granules through a length separator.

10. The method of claim 9, wherein the granules remain free from characteristics which result from a spheronization process, before the granules are subjected to the step of sorting.

11. The method of claim 9, wherein the length separator comprises a surface having cavities formed therein, the surface being arranged to follow a predetermined path such that a granule on the surface, having a predetermined relationship between the dimensions of a given cavity and the length of the granule, will fall and be classified into a given fraction.

12. The method of claim 9, wherein the uncoated, non-spherical granules are prepared by passing a homogenised wet mass through an extruding screen having apertures with predetermined dimensions formed therein; and comminuting the extruded mass to form granules.

13. The method of claim 11, wherein the surface is a cylinder, the predetermined path is rotary about the axis of the cylinder, and a receptacle for collecting the granules to be classified into a given fraction is positioned off-axis of the cylinder.

14. The method of claim 11, wherein the cavities of the surface are each suitable for hosting a single granule of predetermined dimensions.

15. The method of claim 9, wherein at least 80% by number of the selected granules have an aspect ratio greater than 0.7 and less than 2.2.

16. The method of claim 9, further comprising providing the selected granules with a pharmaceutically acceptable coating.

17. The method of claim 9, further comprising subjecting the wherein granules not selected for further processing to further comminuting and sorting according to their aspect ratio.

18. The method of claim 17, further comprising selecting for further processing further comminuted and sorted granules having an aspect ratio greater than 0.7 and less than 2.2.

19. A method for producing a pharmaceutical preparation comprising granules comprising an active pharmaceutical ingredient, comprising using a length separator to select uncoated, non-spherical, extruded granules having an aspect ratio greater than 0.7 and less than 2.2.

20. The method according to claim 19, further comprising applying a pharmaceutically acceptable coating to the selected granules.

21. The method according to claim 19, wherein the length separator comprises a surface having a number of identically pre-shaped cavities formed therein, each cavity being suitable for hosting a single granule, the surface being arranged to follow a predetermined path, so that a granule initially kept in a cavity will fall out of the cavity at a position along the predetermined path, wherein that position depends on the length of the respective granule.

22. The method according to claim 21, wherein the length separator further comprises a collector for collecting granules from at least one predetermined drop-out position to obtain the selection of granules.

23. The method according to claim 22, further comprising applying a pharmaceutically acceptable coating to the selected granules.

24. A pharmaceutical preparation made by the method of claim 9.

25. A pharmaceutical preparation made by the method of claim 16.

26. The pharmaceutical preparation of claim 25, wherein the active pharmaceutical ingredient comprises 5-aminosalicylic acid.

27. A pharmaceutical preparation made by the method of claim 19.

28. A pharmaceutical preparation made by the method of claim 20.

29. The preparation of claim 28, wherein the active pharmaceutical ingredient comprises 5-aminosalicylic acid.

* * * * *